United States Patent
Pardes et al.

(10) Patent No.: US 9,241,828 B2
(45) Date of Patent: Jan. 26, 2016

(54) DELIVERY SYSTEM FOR DISPENSING METERED VOLUMES OF PURE OR STERILE FLOWABLE SUBSTANCES

(75) Inventors: Greg Pardes, New York, NY (US); Paul Mulhauser, New York, NY (US); Lyndon Treacy, Long Island City, NY (US)

(73) Assignee: ReSeal International Limited Partnership, New York, NY (US)

( * ) Notice: Subject to any disclaimer, the term of this patent is extended or adjusted under 35 U.S.C. 154(b) by 0 days.

(21) Appl. No.: 13/066,153

(22) Filed: Apr. 6, 2011

(65) Prior Publication Data

US 2011/0284579 A1 Nov. 24, 2011

Related U.S. Application Data

(60) Provisional application No. 61/341,889, filed on Apr. 6, 2010, provisional application No. 61/458,065, filed on Nov. 17, 2010.

(51) Int. Cl.
| | | |
|---|---|---|
| B65D 37/00 | (2006.01) | |
| A61F 9/00 | (2006.01) | |
| A61M 15/08 | (2006.01) | |
| B05B 11/00 | (2006.01) | |

(52) U.S. Cl.
CPC ............ A61F 9/0008 (2013.01); B05B 11/007 (2013.01); B05B 11/3032 (2013.01); A61M 15/08 (2013.01); B05B 11/0043 (2013.01)

(58) Field of Classification Search
CPC ............................. A61M 15/08; A61F 9/0008
USPC ............ 222/207, 494, 105, 212, 213, 321.7, 222/326, 380, 490
See application file for complete search history.

(56) References Cited

U.S. PATENT DOCUMENTS

| | | | | |
|---|---|---|---|---|
| 2,989,215 | A * | 6/1961 | Willingham | 222/207 |
| 3,220,611 | A * | 11/1965 | Zander et al. | 222/95 |
| 3,715,060 | A * | 2/1973 | Benson | 222/207 |
| 3,902,815 | A * | 9/1975 | Williams | 401/264 |
| 3,963,147 | A * | 6/1976 | Waters | 222/95 |
| 4,308,965 | A * | 1/1982 | Dutt | 215/345 |
| 4,330,071 | A * | 5/1982 | Ohlson | 222/207 |
| 5,044,523 | A * | 9/1991 | McNab | 222/207 |
| 5,836,484 | A * | 11/1998 | Gerber | 222/494 |
| 5,865,795 | A * | 2/1999 | Schiff et al. | 604/70 |
| 5,944,226 | A * | 8/1999 | Schiltz et al. | 222/137 |
| 6,662,977 | B2 * | 12/2003 | Gerber et al. | 222/494 |
| 6,702,155 | B1 * | 3/2004 | Rebne | 222/207 |
| 7,306,129 | B2 * | 12/2007 | Swiss et al. | 222/494 |

(Continued)

Primary Examiner — Donnell Long
(74) Attorney, Agent, or Firm — Kramer Levin Naftalis & Frankel LLP

(57) ABSTRACT

A sealed delivery system for dispensing metered volumes of a pure or sterile flowable substance is presented. Such system comprises a continuously sealing one-way valve assembly at a distal end, and a volume reducing reservoir at a proximal end, in which a pure or sterile flowable substance can be stored. In operation a user pushes down upon an actuator assembly, acting upon a metering pumping chamber in fluid communication with the reservoir via a check valve. Depression of the actuator causes a dispensing pump to push a metered volume of flowable substance through the continuously sealing one way dispensing valve assembly, and return of the actuator to its home state causes the dispensing pump to pull a metered volume of the contained flowable substance from the volume reducing reservoir and through the check valve.

49 Claims, 27 Drawing Sheets

(56) References Cited

U.S. PATENT DOCUMENTS

| | | | |
|---|---|---|---|
| 7,513,396 B2 * | 4/2009 | Pardes et al. | 222/494 |
| 7,678,073 B2 * | 3/2010 | Griffiths et al. | 604/85 |
| 7,726,519 B2 * | 6/2010 | Heldt et al. | 222/153.13 |
| 7,854,352 B2 * | 12/2010 | Davies et al. | 222/162 |
| 7,874,467 B2 * | 1/2011 | Pardes et al. | 222/494 |
| 7,931,173 B2 * | 4/2011 | Yuan | 222/207 |
| 7,997,453 B1 * | 8/2011 | Gallegos | 222/207 |
| 7,997,460 B2 * | 8/2011 | Pardes et al. | 222/494 |
| 8,006,870 B2 * | 8/2011 | Stadelhofer et al. | 222/207 |
| 8,087,553 B2 * | 1/2012 | Pardes et al. | 222/494 |
| 2006/0191959 A1 * | 8/2006 | Davies et al. | 222/162 |
| 2009/0218373 A1 * | 9/2009 | Pardes et al. | 222/494 |
| 2009/0236374 A1 * | 9/2009 | Pardes et al. | 222/494 |
| 2012/0111899 A1 * | 5/2012 | Pardes et al. | 222/494 |

* cited by examiner

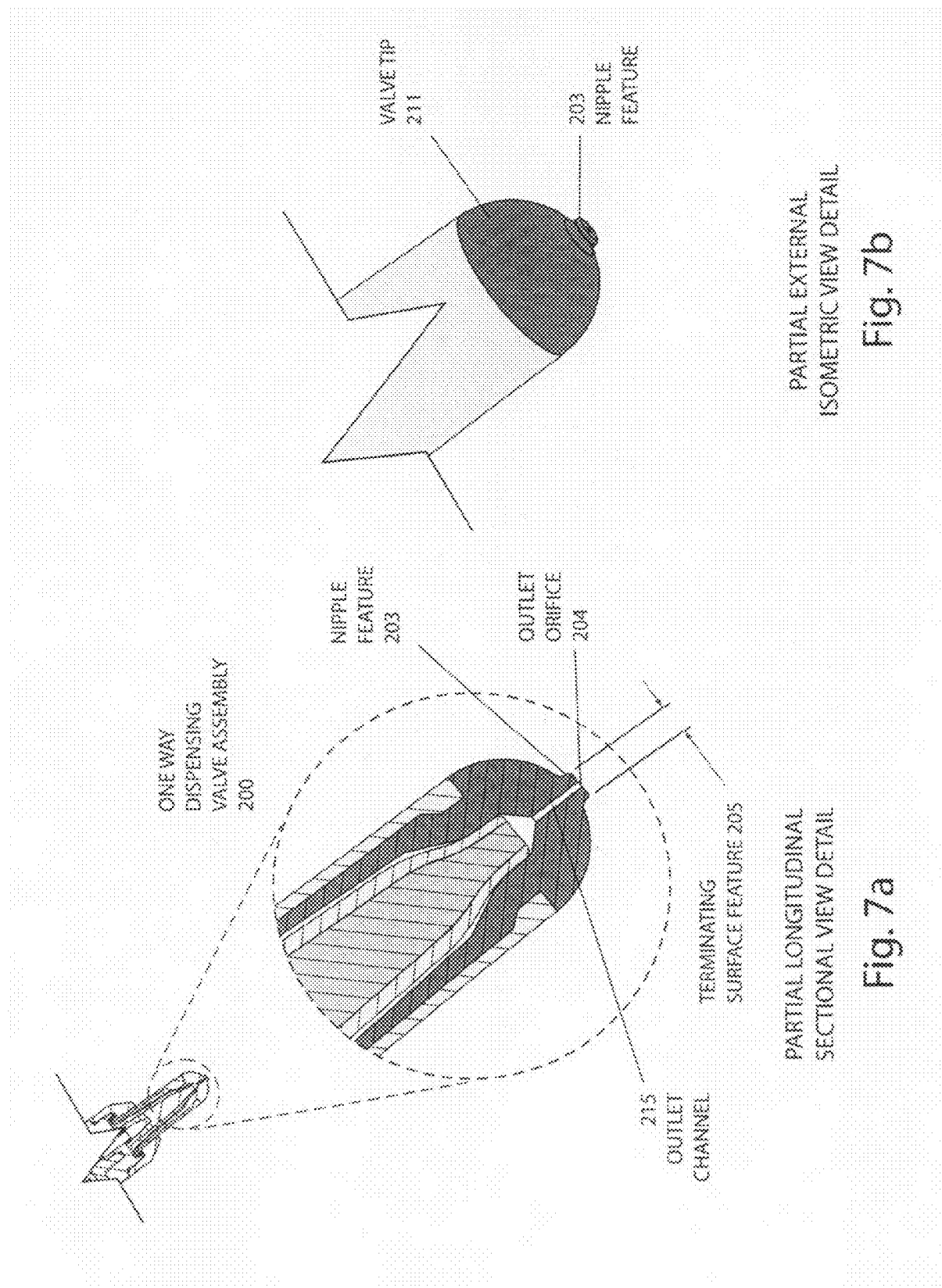

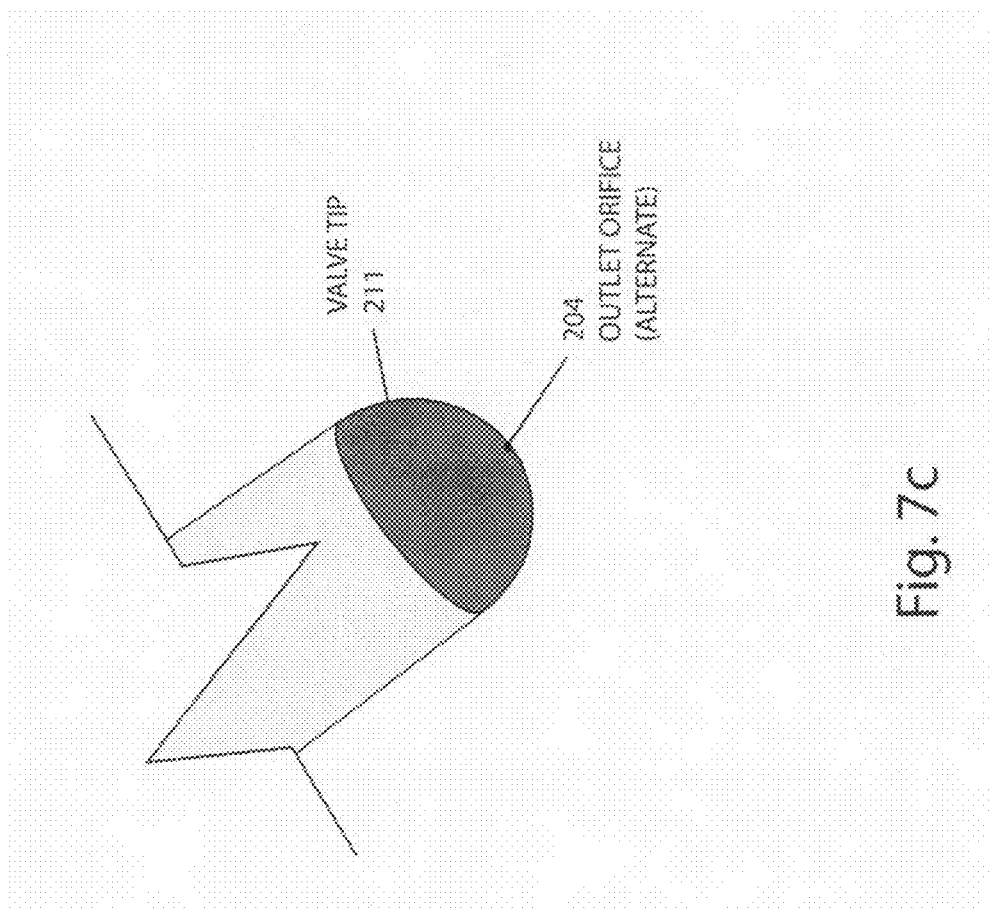

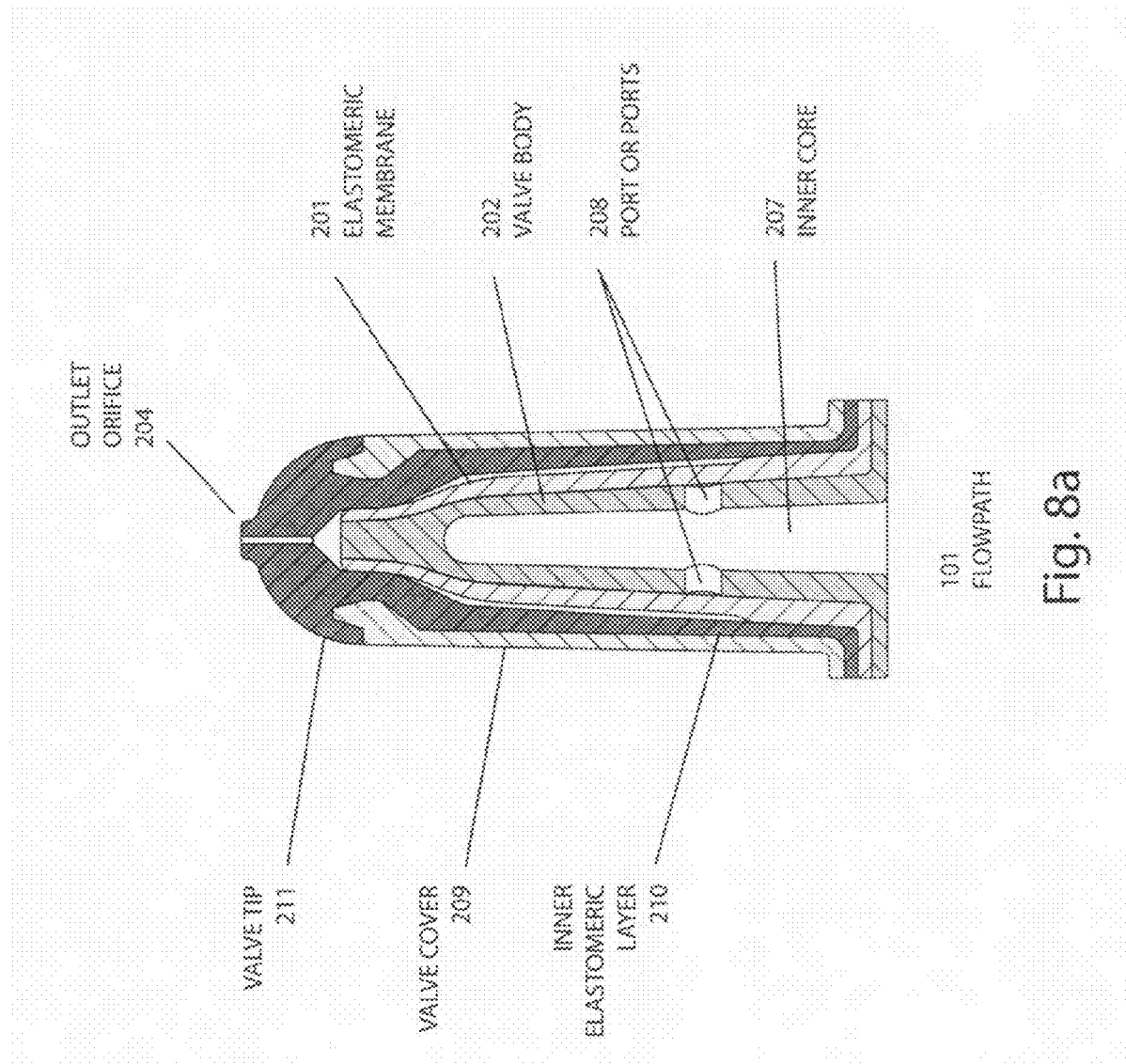

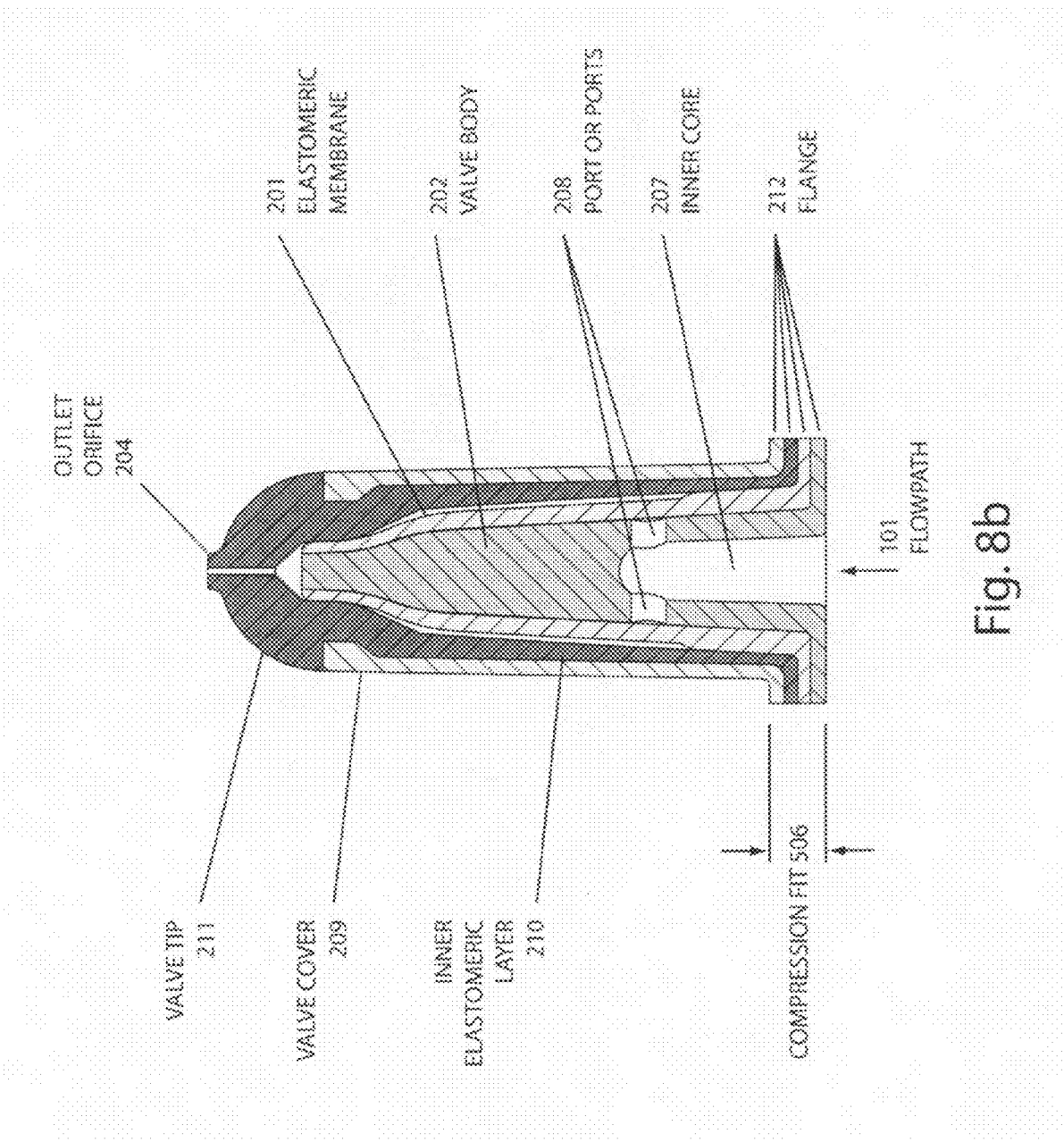

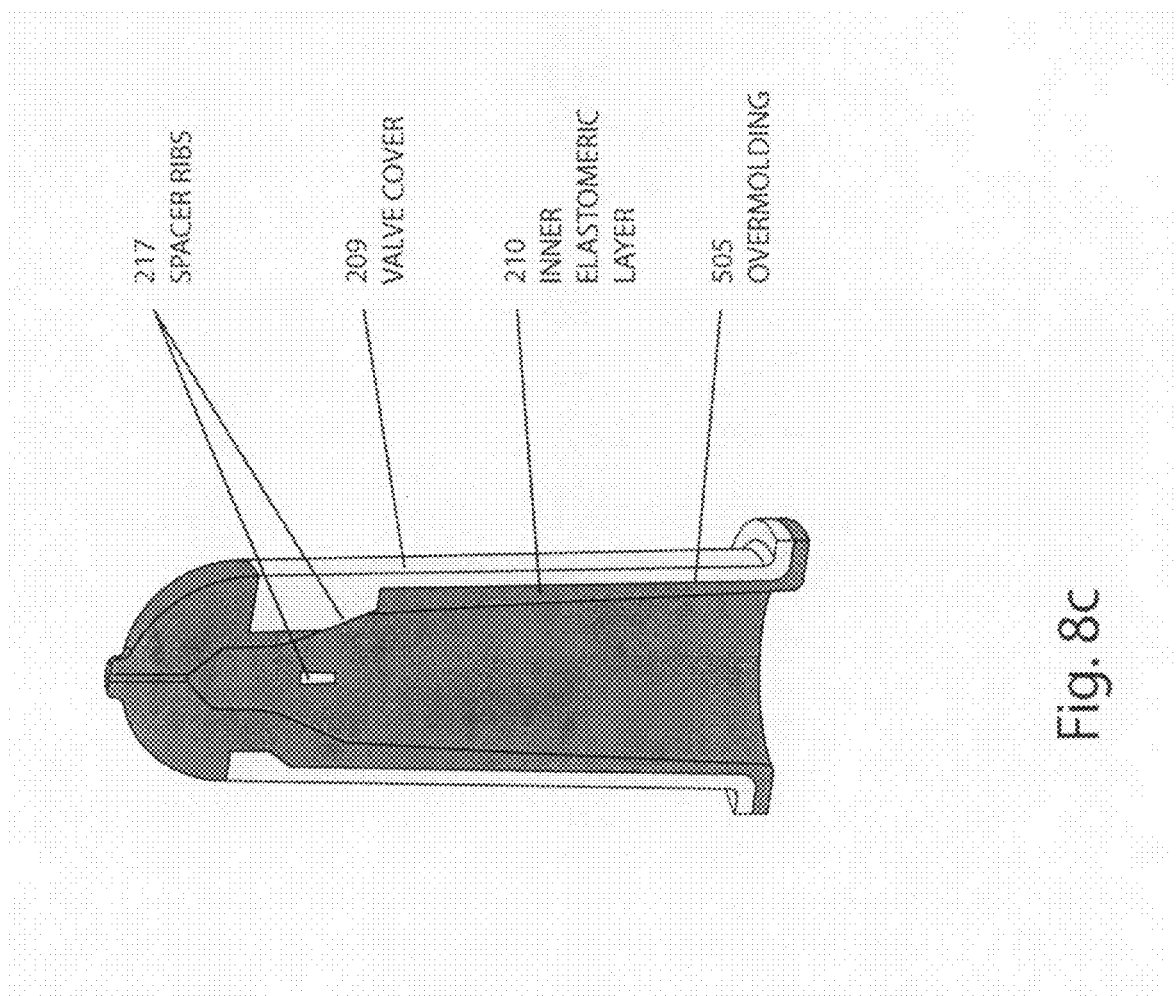

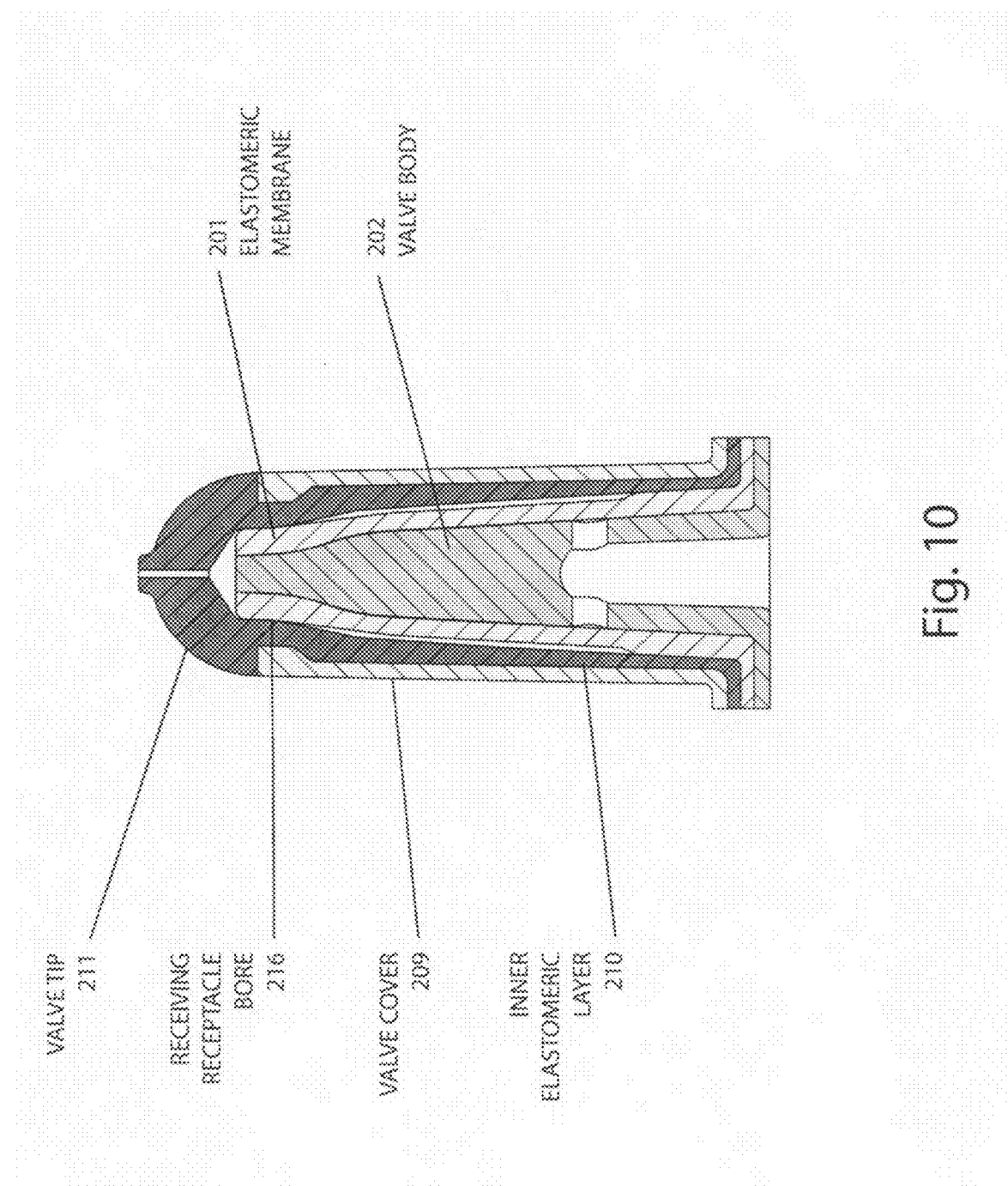

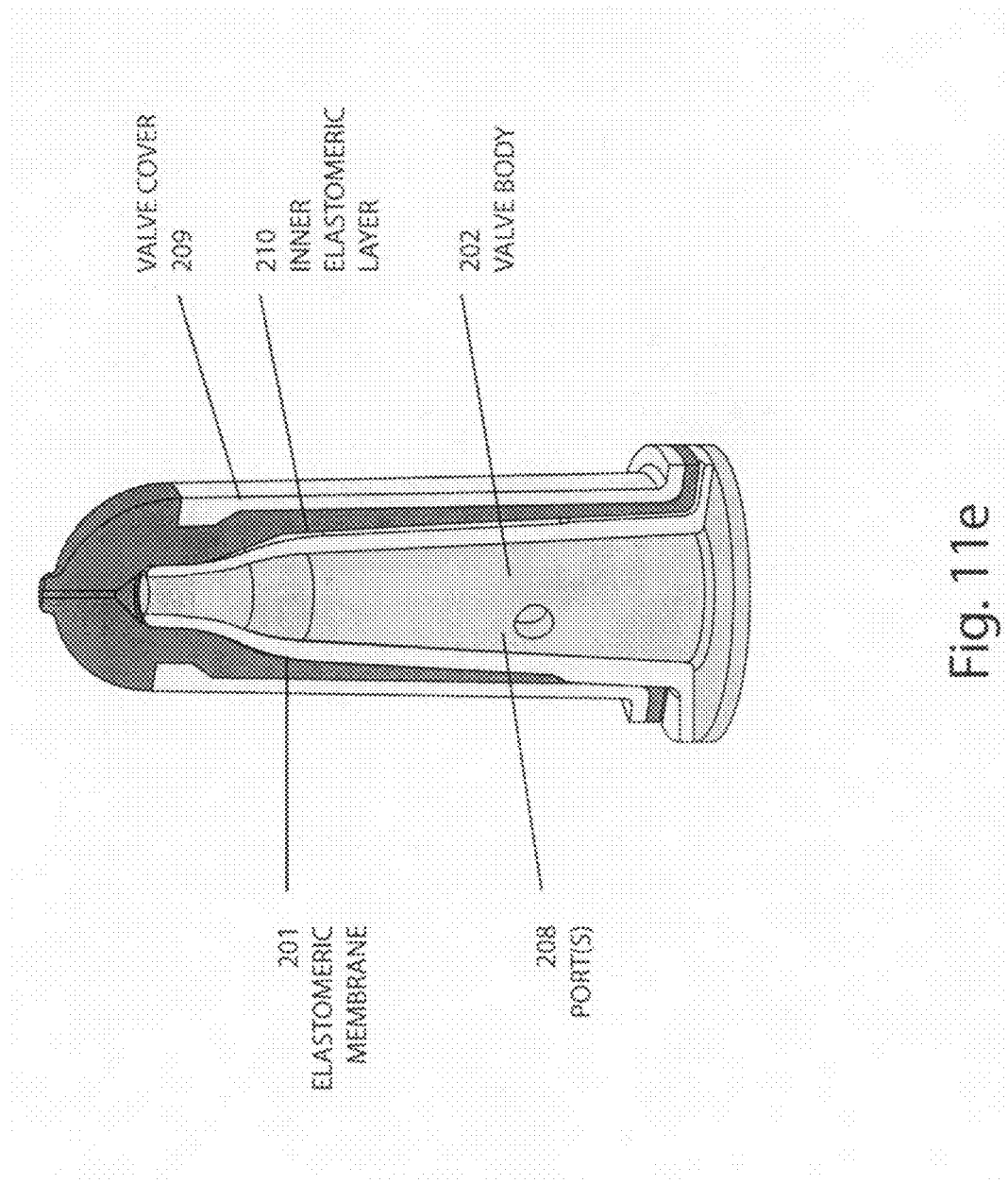

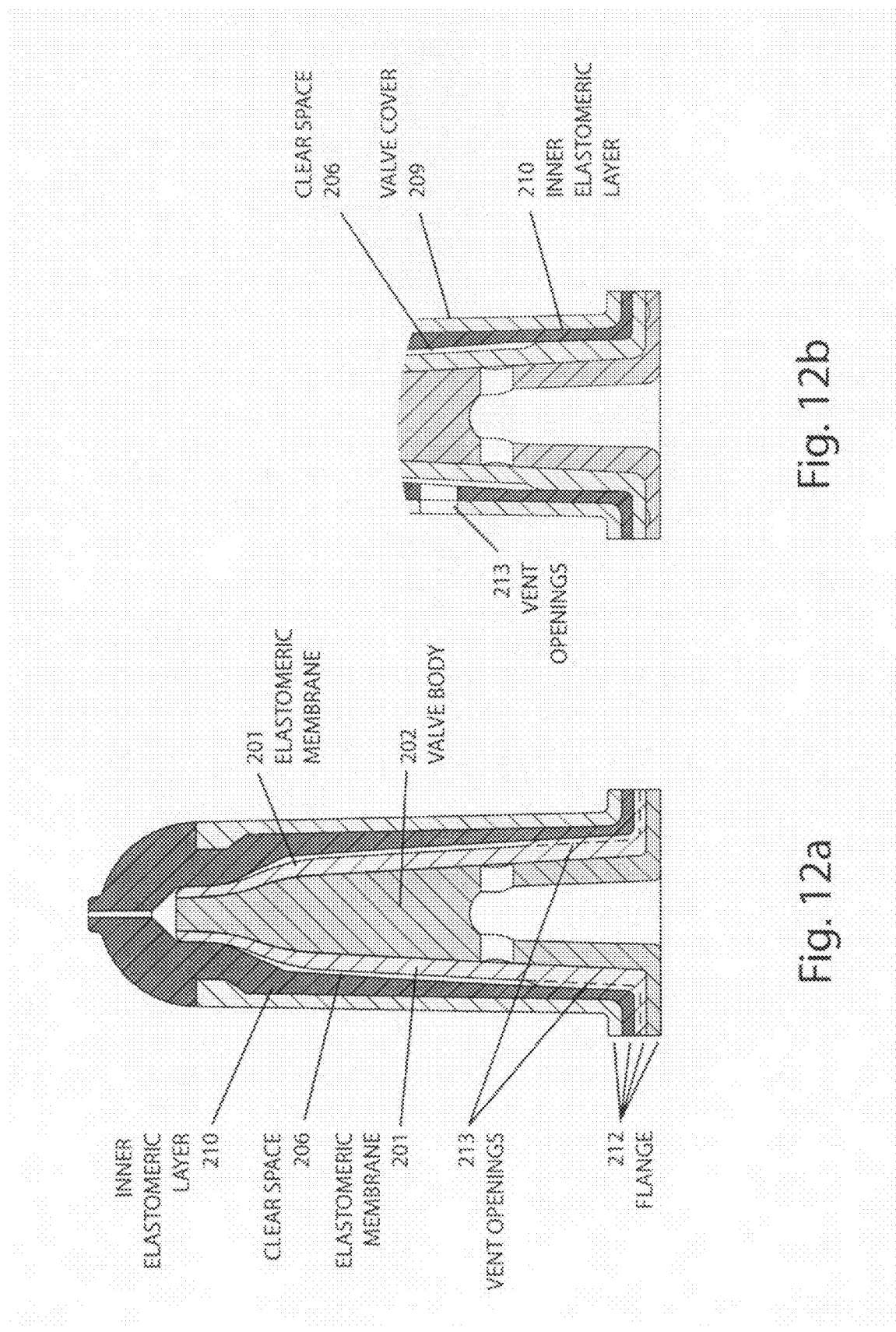

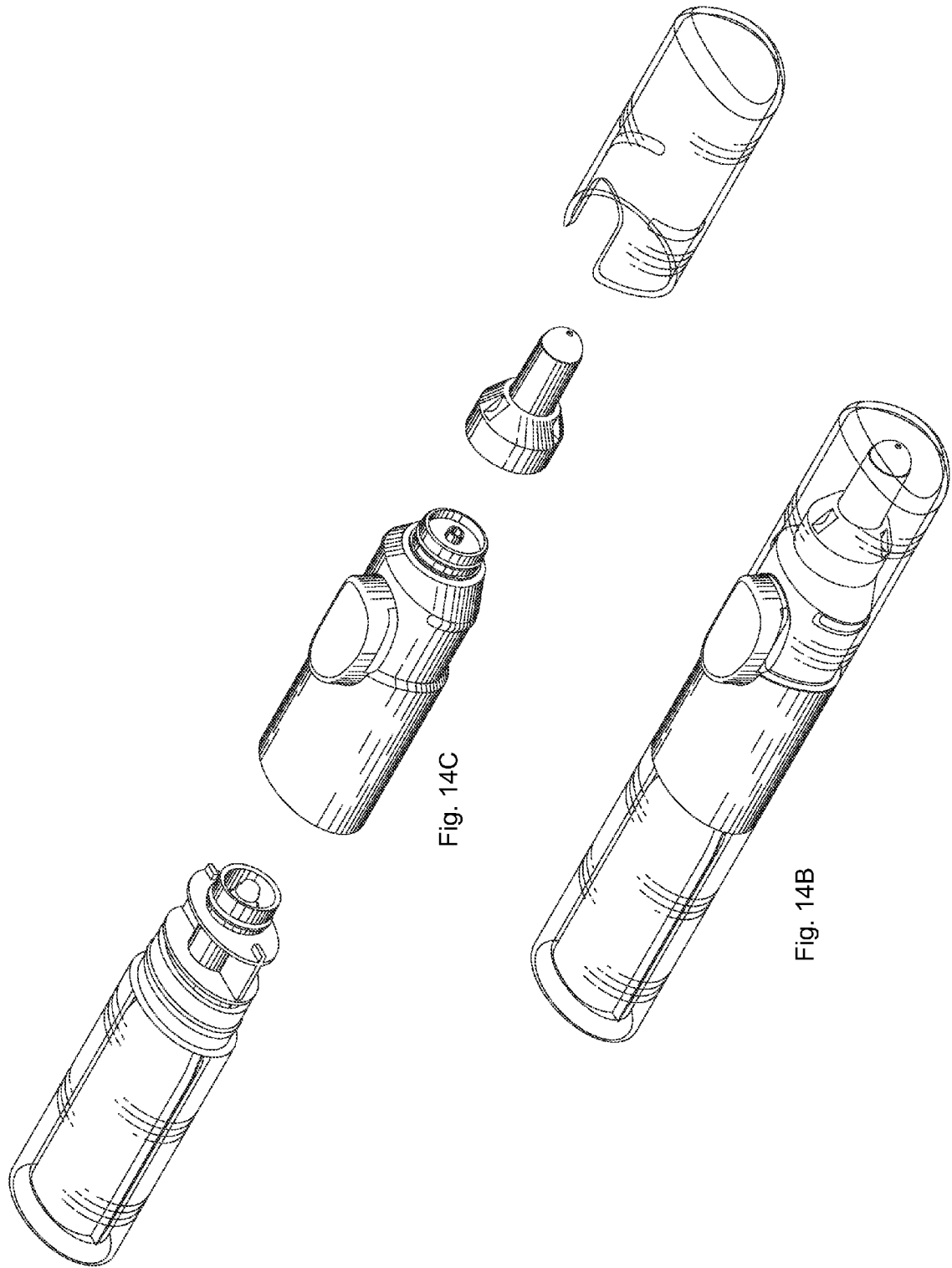

DELIVERY SYSTEM FOR DISPENSING METERED VOLUMES OF PURE OR STERILE FLOWABLE SUBSTANCES

CROSS-REFERENCE TO RELATED APPLICATIONS

This application claims the benefit of U.S. Provisional Patent Applications Nos. 61/458,065, filed on 17 Nov. 2010, and 61/341,889, filed on 6 Apr. 2010, the disclosures of which are hereby fully incorporated herein by reference.

TECHNICAL FIELD

The present invention is directed to a delivery system for dispensing a flowable substance, and in particular to a hand-held delivery system for the metered dispensing of pure or sterile flowable substances that is suitable for dispensing preservative-free multiple dose preparations, including a compressible pumping chamber and a continuously sealing one way valve assembly.

BACKGROUND THE INVENTION

Conventionally, in order to maintain a flowable substance free of contaminants, preservatives have been added to the flowable substance. However, the use of preservatives tends to be detrimental to many users and can often limit the effectiveness of the flowable substance. Over time and through repeated use they are even likely to be harmful, as they are absorbed through one or more of a patient's or user's mucous membranes, orifices, skin, etc., particularly when the flowable substance is a pharmaceutical such as, for example, an eye care solution, an intranasal drug or moisturizer, a cosmetic treatment or a skin treatment product. Nonetheless, this type of product is most often formulated with preservatives. Of course the flowable substance may also be, for example, a foodstuff, beverage, nutraceutical or cosmeceutical product, all of which are generally formulated with preservatives. As is becoming more and more well known, such preservatives can have a variety of long standing harmful effects. For example, the well known preservative benzylkonium chloride, or BAK, which has been used in a wide variety of pharmaceutical preparations since the 1930s and 1940s, and is currently used in numerous glaucoma therapeutics, turns out to exhibit "very significant toxicity and the production of inflammatory mediators." Fechtner, Robert D., Asbell, Penny A. and Kahook, Malik Y., *Ocular Surface Disease in the Presence of Glaucoma*, Supplement to Glaucoma Today and Advanced Ocular Care, February March 2011 at 6. In fact, "preservatives are the number one-cause of worsening dry eye disease and OSD as well as of perpetuating patients' pain syndrome." Id. at 5. Similarly, in describing BAK as the most common preservative in ophthalmic preparations, Dr. Herbert L. Gould noted "[i]t has well been demonstrated that this chemical, while moderately bactericidal, is highly toxic to the cornea and conjunctiva as well as to nasal mucous membrane." Gould, Herbert L., MD, *Solving the Preservative Paradox*, Opthalmology Management, August 2006, 47-52, at 47. "When solutions containing this preservative are frequently applied, serious tissue damage has been reported." Id. The article goes on to describe how long term use of eye drops with BAK has been shown to cause, inter alia, cataracts and maculopathy, damage to epithelial cells, inflammation and damage to the cornea. Id. at 47-52. What is yet to be studied is the cumulative effect on middle age and elderly persons of using multiple preparations, each containing various and sundry preservatives, over years and even decades. It may very well be that the cumulative negative effects of the preservatives, on balance, outweighs any beneficial effect of the pharmaceuticals and other flowable substances being used and ingested.

Another consideration in the dispensing or delivery of a flowable substance is the ability of a delivery system to deliver a selected amount of a flowable substance to its intended destination without causing any damage to the user, such as, for example, when applying an eye care solution directly into the eye without introducing any contamination.

In the past, flexible membranes have been used to control the flow of such a flowable substance to a valve assembly outlet while preventing any backflow to the source of the flowable substance. However, such valves (such as, for example, the valve type described in U.S. Pat. No. RE 34,243) involve the use of O-rings in conjunction with a uniformly thick flexible membrane to effect a seal. This is cumbersome to manufacture and assemble. Other valve assemblies require squeezing a reservoir of flowable substance in order to dispense the flowable substance. Such squeezing can be difficult for the very young—or the very old—as well as for physically challenged or disabled individuals.

Therefore, an effectively designed and easy to operate valve assembly and easily actuated metering delivery system for delivering or dispensing pure or sterile, preservative-free flowable substances is highly desirable. Further, such a delivery system should be capable of being manufactured economically, by (i) reducing the costs of component parts and (ii) allowing the use of high speed automated production, which itself is also required by many regulators.

Thus, what is needed in the art is a delivery system and method for the metered dispensing and maintenance of preservative-free flowable substances in a multi-dose format, that at the same time can prevent contamination in the delivery or dispensing system, that can solve the above-described problems of the prior art.

SUMMARY OF THE INVENTION

Systems for the delivery or dispensing of a flowable substance, including, for example, a one way dispensing valve, are presented. Such systems can utilize any type of highly effective one way dispensing valve and/or a contaminant limiting material within the flow path to the dispensing orifice. In exemplary embodiments of the present invention, a pure[1] or sterile flowable substance can, for example, be preservative-free and the delivery system can prevent any backflow of contaminants into the source of the flowable substance. Thus, such a delivery system can deliver such a flowable substance in a multi-dose and preservative-free format. In exemplary embodiments of the present invention, the delivery system can include, for example, a valve assembly enclosed by a pressure displaceable flexible elastomeric membrane for effecting the passage of the flowable substance to a controllable outlet, while preventing any backflow to the source of the flowable substance after dispensing individual portions or doses of the flowable substance. In exemplary embodiments of the present invention, the tip and other portions of the delivery system can be made to be bacteriostatic, bactericidal, or both. In exemplary embodiments of the present invention, the valve assembly can, for example, work in conjunction with a push button metered dispensing pump to dispense individual portions or doses of the flowable substance. In exemplary embodiments of the present invention, the sealed delivery system can prevent the ingress of any possible contaminants, such as, for example, microbes, including, for example, bacteria, yeasts, molds, fungi, etc.

[1] It is noted that the term "pure" as used herein is understood to include any aseptic substance.

BRIEF DESCRIPTION OF THE DRAWINGS

FIG. 7a is a locally viewed enlarged partial longitudinal sectional detailed view through an exemplary nipple feature according to an exemplary embodiment of the present invention;

FIG. 7b is a locally viewed partial external isometric detailed view of the nipple feature detail of FIG. 7a;

FIG. 7c is a locally viewed partial external isometric detailed view the tip of a continuously sealing one way dispensing valve assembly without any nipple feature;

FIG. 8a is an axially extending view of a continuously sealing one way dispensing valve assembly having an extended inner core at rest according to an exemplary embodiment of the present invention;

FIG. 8b is a longitudinal cross-sectional view of a continuously sealing one way dispensing valve assembly having a truncated inner core at rest according to an exemplary embodiment of the present invention;

FIG. 8c is a longitudinal cross-sectional isometric view of the valve cover and inner elastomeric layer of the continuously sealing one way dispensing valve assembly of FIGS. 8a and 8b showing detail of spacer ribs extending inwards from the valve cover through the inner elastomeric layer according to an exemplary embodiment of the present invention;

FIG. 10 is an exemplary view of the continuously sealing one way dispensing valve assembly shown with an elastomeric membrane that becomes progressively thicker distally;

FIG. 11e is a longitudinal partial cross sectional perspective view through a one way dispensing valve assembly as shown in FIG. 11a according to an exemplary embodiment of the present invention showing various structures;

FIGS. 12a-12b are exemplary views of the continuously sealing one way dispensing valve assembly of FIGS. 9 and 10 shown with alternative types of vent openings to facilitate movement of the elastomeric membrane;

FIG. 14b depicts an exterior view of the exemplary system of FIGS. 1-3;

FIG. 14c depicts the exemplary system of FIGS. 1-3 broken into fully assembled subassemblies;

DETAILED DESCRIPTION OF THE INVENTION

In exemplary embodiments of the present invention, a delivery system is provided for dispensing specifically metered volumes of pure or sterile flowable substances while preventing any backflow of contaminants into the source of the flowable substance, thereby eliminating the need for the use of preservatives. In contrast to prior art devices, such exemplary delivery systems thus allow the dispensing of multiple doses from one device, without contamination and without preservatives or the like.

In such an exemplary delivery system a continuously sealing one way dispensing valve assembly can be provided at the distal end of a delivery system. Through such valve a pure or sterile flowable substance can be pushed, for example, by the manual compression of a metered volume confined within a dispensing pump, which, when returning to a decompressed or "home" state can, for example, withdraw or pull a next metered volume of the flowable pure or sterile substance through a one-way check valve from a volume reducing reservoir. Once pulled through the check valve into the dispensing pump, the metered volume of the pure or sterile flowable substance is ready for further-dispensing. The check valve can, for example, be provided at the distal end of the volume reducing reservoir and upstream of the dispensing pump chamber, and (i) the continuously sealing one way dispensing valve assembly, (ii) the dispensing pump, (iii) the check valve and (iv) the volume reducing reservoir can, for example, all be in sealed contact with each other, collectively comprising a sealed fluid conveying flowpath within the delivery system.

Figure 1:
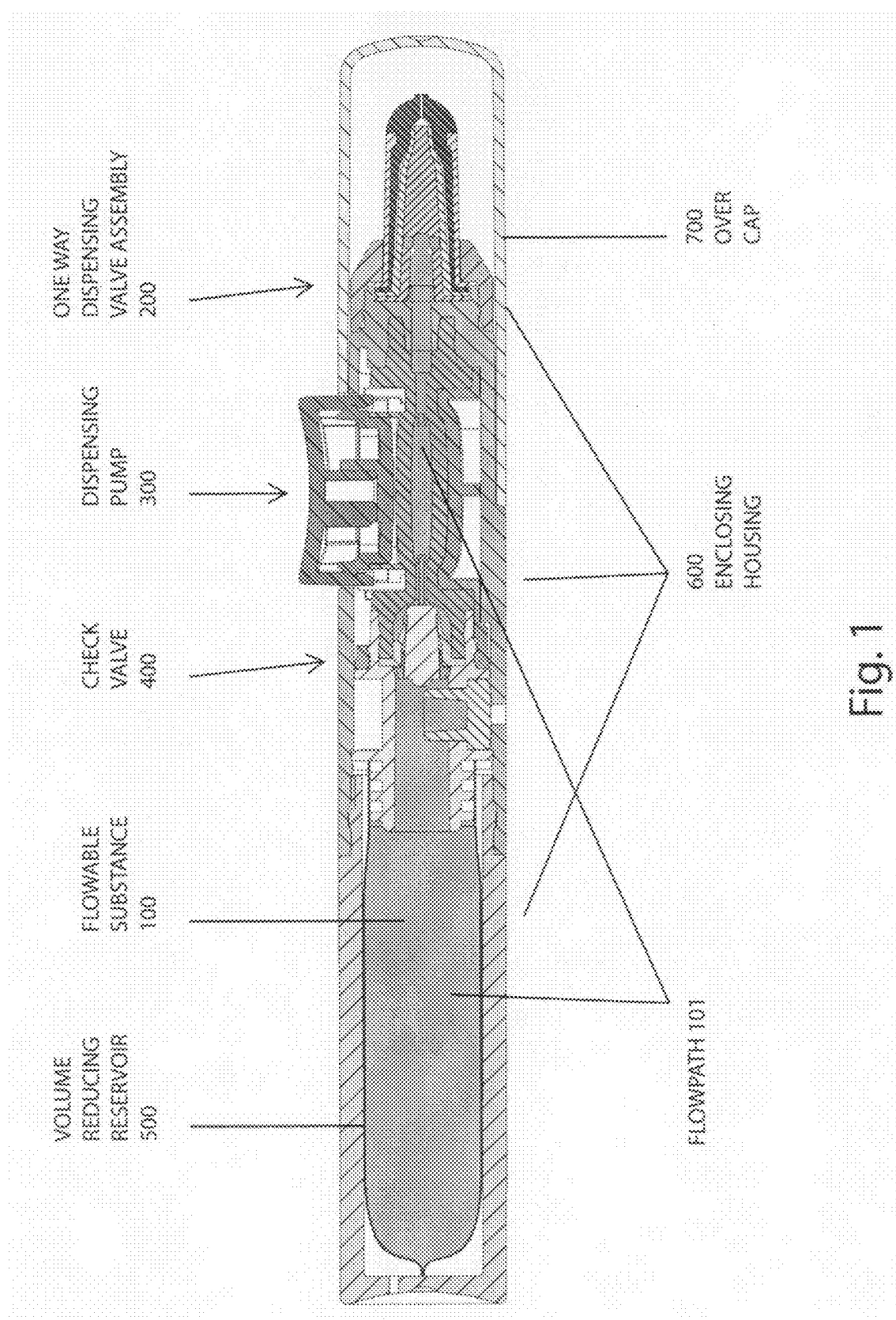
FIG. 1 is a longitudinal cross sectional view of an exemplary embodiment of the present invention, noting basic subsystems.
Figure 2:
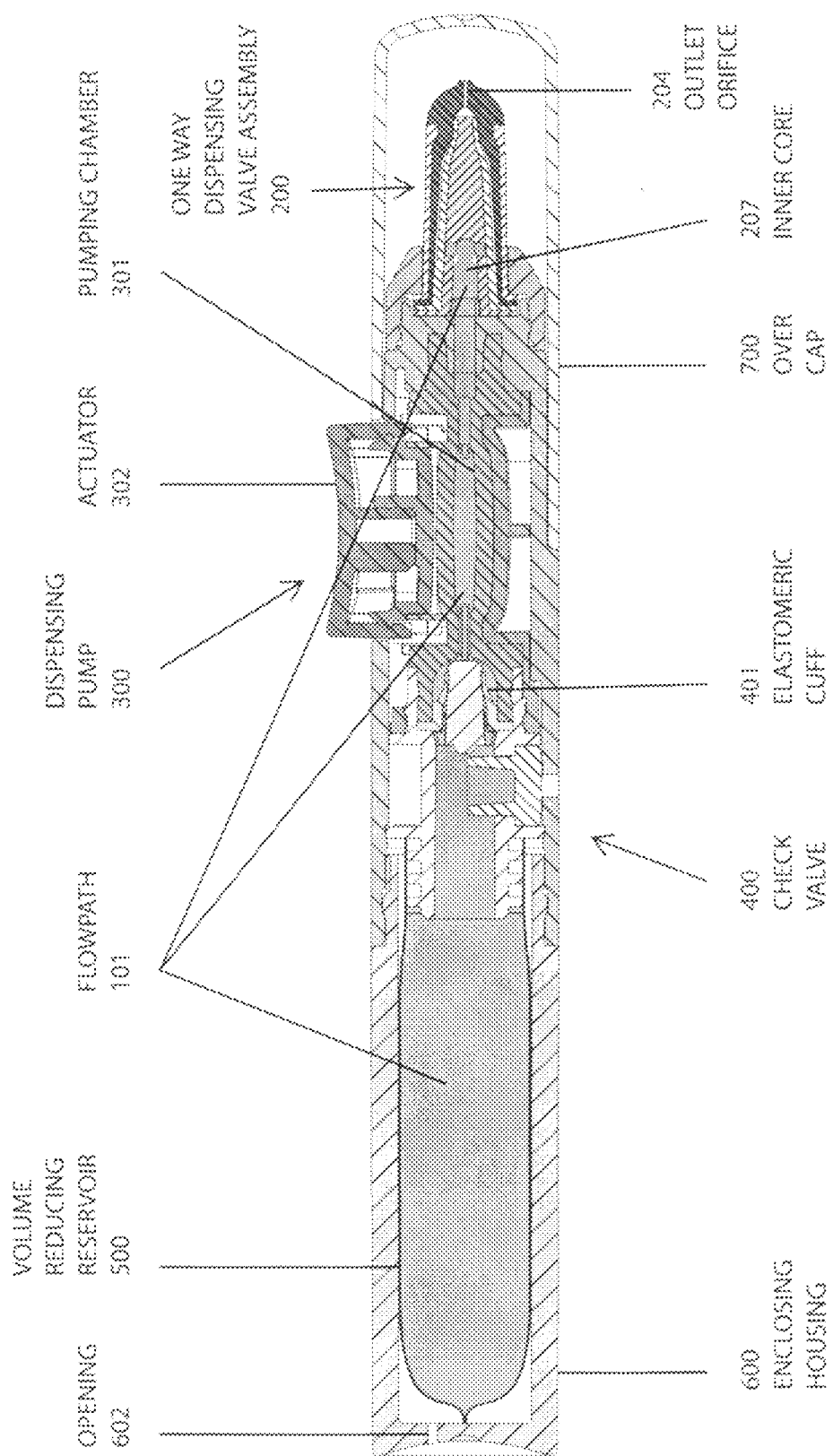
FIG. 2 is a longitudinal cross sectional view of FIG. 1 showing further details.
Figure 3:
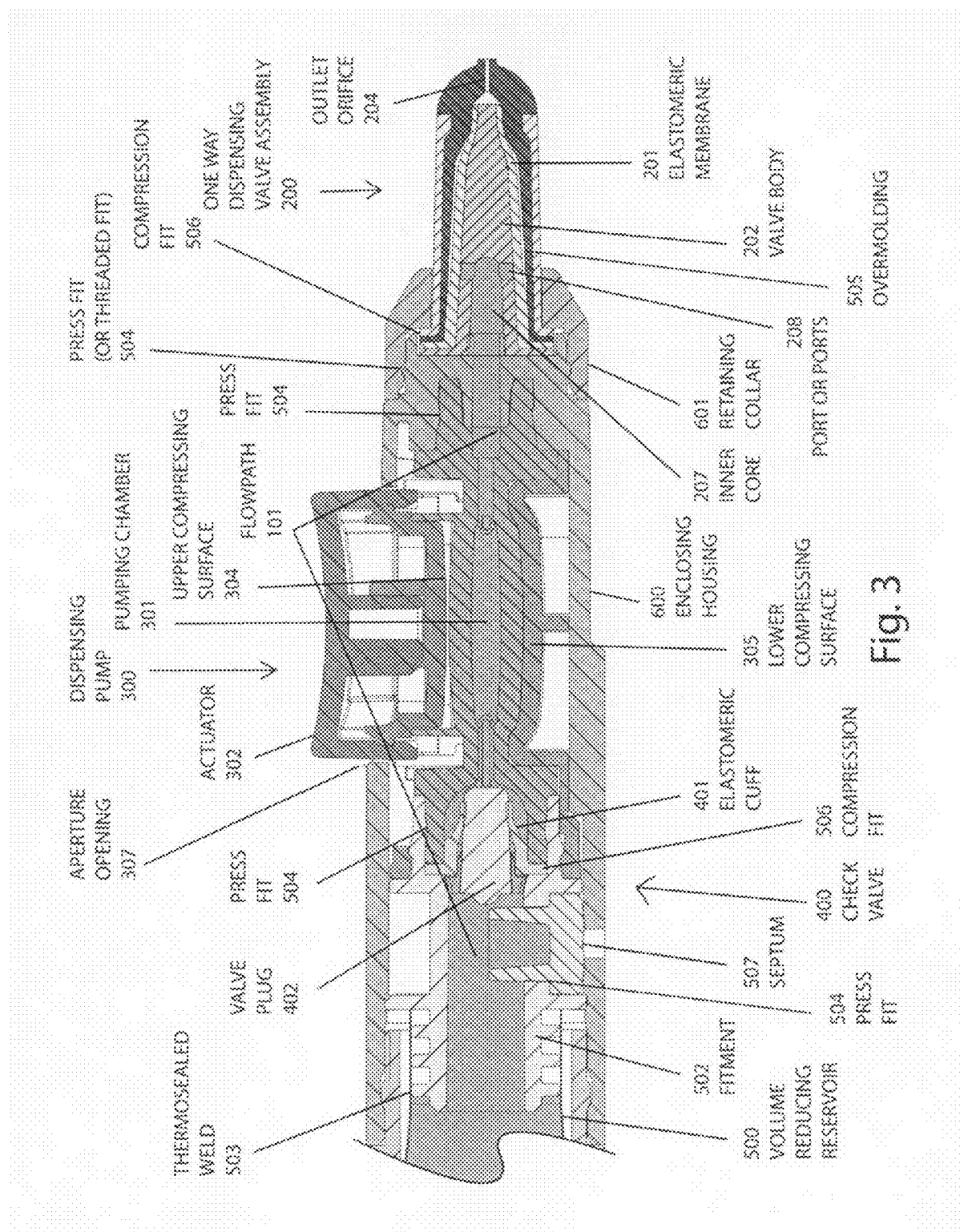
FIG. 3 is an enlarged partial axially extended cross sectional view of the right (distal) portion of FIG. 2 showing additional details.

An exemplary system for delivering or dispensing metered volumes of a flowable pure or sterile substance according to exemplary embodiments of the present invention is shown in FIGS. 1-3, which are next described.

FIG. 1 depicts a longitudinal cross sectional view of an exemplary delivery system showing the overall assembly, and indicating a sealed fluid conveying pathway containing a pure or sterile flowable substance 100, according to an exemplary embodiment of the present invention. While the present invention is intended to provide the ability to maintain and deliver pure or sterile contents, it is also noted that various exemplary embodiments can also be used to dispense metered volumes of non-pure or non-sterile flowable solutions as well (the use of the exemplary system will simply prevent any (additional) contamination from the outside environment). With reference to FIG. 1, the delivery system can deliver or dispense, for example, metered volumes of a pure or sterile flowable substance 100 from a hand-held delivery system comprising a one way dispensing valve assembly 200. As shown in FIG. 1 (and in FIGS. 2-3 as well), the exemplary delivery system can, for example, also include dispensing pump 300, check valve 400, volume reducing reservoir 500, enclosing housing 600 and overcap 700.

With reference to FIG. 2, the one way dispensing valve assembly 200 is shown at the distal end of the delivery system, through which flowable substance 100 can be pushed by, for example, the manual compression of a metered volume confined within dispensing pump 300 which, when returning to a decompressed state can, for example, withdraw or pull a next metered volume of flowable substance 100 through check valve 400 from volume reducing reservoir 500. It is noted that non-manual mechanized or motorized dispensing pumps can, for example, also be used. Once pulled through check valve 400 into dispensing pump 300, such next metered volume of the flowable substance 100 is, for example, ready for further dispensing. Check valve 400 can be, for example, provided at the distal end of the volume reducing reservoir 500, as shown in FIG. 2.

As noted, one way dispensing valve assembly 200, dispensing pump 300, check valve 400 and volume reducing reservoir 500 can, for example, all be in sealed contact with each other, comprising a sealed fluid conveying flowpath 101 to isolate and protect the pure or sterile substance contained within from ingress of external contaminants—such as, for example, microbes, including, for example, bacteria, yeasts, molds, fungi, etc. The components comprising the sealed flowpath 101 can, for example, be made with materials which create a barrier to external contamination, such as, for example, bacteriostatic and/or bactericidal materials and coatings, as described below.

Additionally, for example, the delivery system materials and assembly methods can also be specified to provide a barrier against moisture vapor or oxygen penetration. To assure secure assembled seals preventing any undesirable ingress or inadvertent user defeat, the connection of all interfacing components comprising flowpath 101 can, for example, as shown in FIG. 3, be securely affixed and sealed with the use of designed features and manufacturing processes. These can include, for example, thermosealed welds 503, interference or press fits 504, two-shot molding or overmolding 505, compression fits 506, ultrasonically welded assembly, or adhesive bonding. In preferred embodiments, such components can be manufactured to very close tolerances to ensure intimately touching or interference or sealed closures so as to preventingress of bacteria, fungi, yeast, molds and other similar microbial contaminants into the flowable substance 100 within flowpath 101.

Continuing with reference to FIG. 2, volume reducing reservoir 500 can be, for example, a sealed component which reduces proportionally in size to the amount of flowable substance 100 that is withdrawn or pulled from it, thereby preventing ingress of external contaminants. Volume reducing reservoir 500 can, for example, be a collapsible bellows, concertina, tube, bag, pouch or other type of form designed to dispense practically all of its contents without creating an internal vacuum. Reservoir 500 can be, for example, encased or shielded within an enclosing housing 600 to prevent uncontrolled changes to its contained volume from the application of accidental pressures or other outside physical influences. It is noted that enclosing housing 600 can have one or more vents or openings 602 to allow ambient pressure to fill the space exterior to volume reducing reservoir 500 resulting from the evacuation of product from the delivery system. Such vents 602 or openings allow air to enter between the inner surface of enclosing housing 600 and the outer surface of volume reducing reservoir 500, thus allowing the volume reducing reservoir to contract as flowable substance 100 is dispensed. Alternatively, for example, other means can be used to achieve the reduction of reservoir volume, such as, for example, a movable compliant piston within a rigid tubular reservoir. In exemplary embodiments of the present invention, reservoir 500 can, for example, be a formed pouch made with, for example, a foil, or a PET type polymer having high moisture and vapor barrier properties, coextruded with an internal LDPE film surface for heat seal adhesion. Reservoir 500 can, for example, be appropriately sized for any particular flowable substance 100 to be dispensed, and thus, can hold, for example, 5 ml, 10 ml, 15 ml, etc. volumes of flowable substance 100 in various exemplary embodiments.

FIG. 3 is an enlarged view of the right (distal) portion of FIG. 2 showing greater detail. In the exemplary embodiment of the present invention shown in FIG. 3, the only orifice available to sealed flowpath 101 is outlet orifice 204, which provides an exit path from one way dispensing valve assembly 200. Thus, one way dispensing valve assembly 200 can, for example, convey flowable substance 100 from volume reducing reservoir 500 while preventing any backflow of contaminants into any flowable substance 100 that may be contained within flowpath 101 and volume reducing reservoir 500 after a specified portion of flowable substance 100 has been dispensed.

Continuing with reference to FIG. 3, in operation, dispensing pump 300 can, for example, pull a metered volume of contained flowable substance 100 from volume reducing reservoir 500 out through check valve 400. Dispensing pump 300 can include, for example, a compressible pumping chamber 301, sized to displace a specific volume of flowable substance 100 as may be desired for a specific application. For example, the displaced volume of pumping chamber 301 for dispensers delivering a metered volume of particular eye care solutions may be sized to, for example, as little as 20 microliters or as large as 50 microliters. In exemplary embodiments of the present invention, pumping chamber 301 can be, for example, elastomeric. Pumping chamber 301 can, for example, be configured as a squeeze bulb, concertina, bellows or other controllably collapsible form. When pumping chamber 301 is compressed, the metered volume contained within it can be, for example, pushed through one way dispensing valve 200 and out to, for example, a patient or user. When returning to its static decompressed state, pumping chamber 301 pulls a metered volume of flowable substance 100 from volume reducing reservoir 500 to refill pumping chamber 301 with the evacuated metered quantity.

As noted, in exemplary embodiments of the present invention, check valve 400 can, for example, be positioned between pumping chamber 301 and volume reducing reservoir 500, causing unidirectional flow (distally) as pumping chamber 301 pulls each metered volume, via negative pressure, from volume reducing reservoir 500, and subsequently pushes the metered volume with positive pressure through one way dispensing valve assembly 200. In particular, a subsequent compression of pumping chamber 301 after an initial metered dosing pushes and displaces flowable substance 100 remaining in inner core 207 of one way dispensing valve assembly 200 after the previous dosing out through outlet orifice 204. Thus, inner core 207 is logically an extension of pumping chamber 301, and thus all flowable substance 100 forward (distal) of check valve 400 communicates as one volume when pressure is applied to dispensing pump 300. Continuing in this manner, the dispensing of individual portions of flowable substance 100 can be continued until volume reducing reservoir 500 is completely emptied.

In exemplary embodiments of the present invention, check valve 400 can, for example, be any of a number of various types of check valves, such as, for example, a duck-bill valve, disk valve, ball valve, or umbrella valve. In exemplary embodiments of the present invention check valve 400 can, for example, have a cylindrical elastomeric cuff 401 that can, for example, be molded with a low durometer compliant thermoplastic elastomer (e.g., TPE) or silicone and be stretched around cylindrical valve plug 402, to form a one-way seal. In operation, decompression of pumping chamber 301 creates negative pressure on the distal end of check valve 400, which expands elastomeric cuff 401, thus enabling flowable substance 100 to be pulled between elastomeric cuff 401 and valve plug 402 from reservoir 500 into pumping chamber 301. Subsequent compression of pumping chamber 301 creates positive pressure upon the flowable substance 100 contained within, which pushes downwards upon elastomeric cuff 401, causing it to seal firmly against valve plug 402, thus precluding retro-flow back into reservoir 500.

It is noted that there are various alternative ways known to one skilled in the art to assemble and interconnect reservoir 500, check valve 400 and pumping chamber 301 in a manner so as to ensure a secure sealed flow path 101. With reference to FIG. 3, reservoir 500, here shown, for example, as a formed collapsible pouch, when made with, for example, a low density polyethylene (LDPE) coextruded lining, can be ultrasonically or heat welded upon the proximal end of an injection molded LDPE plastic fitment 502 to achieve, for example, a continuous thermosealed weld 503. Pumping chamber 301, comprised as shown, for example, of a flexible thermoplastic elastomer, can, for example, be attached with a press fit 504 into (or alternatively onto) a mating feature on the distal end of such fitment 502. Check valve 400 can be included or captured as shown, for example, between fitment 502 and pumping chamber 301. Additionally, a septum 507, for example, molded with silicone or a thermoplastic elastomer (e.g., TPE), can be press fit into a hole in fitment 502. Septum 507 can, for example, create a portal to and sealed barrier between the outer environment and the portion of flowpath 101 within reservoir 500 and proximal to check valve 400. To be used as a portal, septum 507 can be pierced, for example, with a sharp hollow sterile needle, providing an aseptic path and means to fill reservoir 500, and then continue to fill through the check valve 400, pumping chamber 301, and dispensing valve assembly 200 until the entire fluid conveying flowpath 101 has been filled with flowable substance 100. Septum 507 can then, for example, self-reseal upon removal of such sterile needle. Use of an elastomeric septum 507 in this manner is common practice among fluidic systems used for medical applications. In exemplary embodiments of the present invention the septum can be arranged to be single-use, such as, for example, by being covered with an affixed cap, after filling, so as to prevent user attempted refilling and/or contamination.

Figure 4:
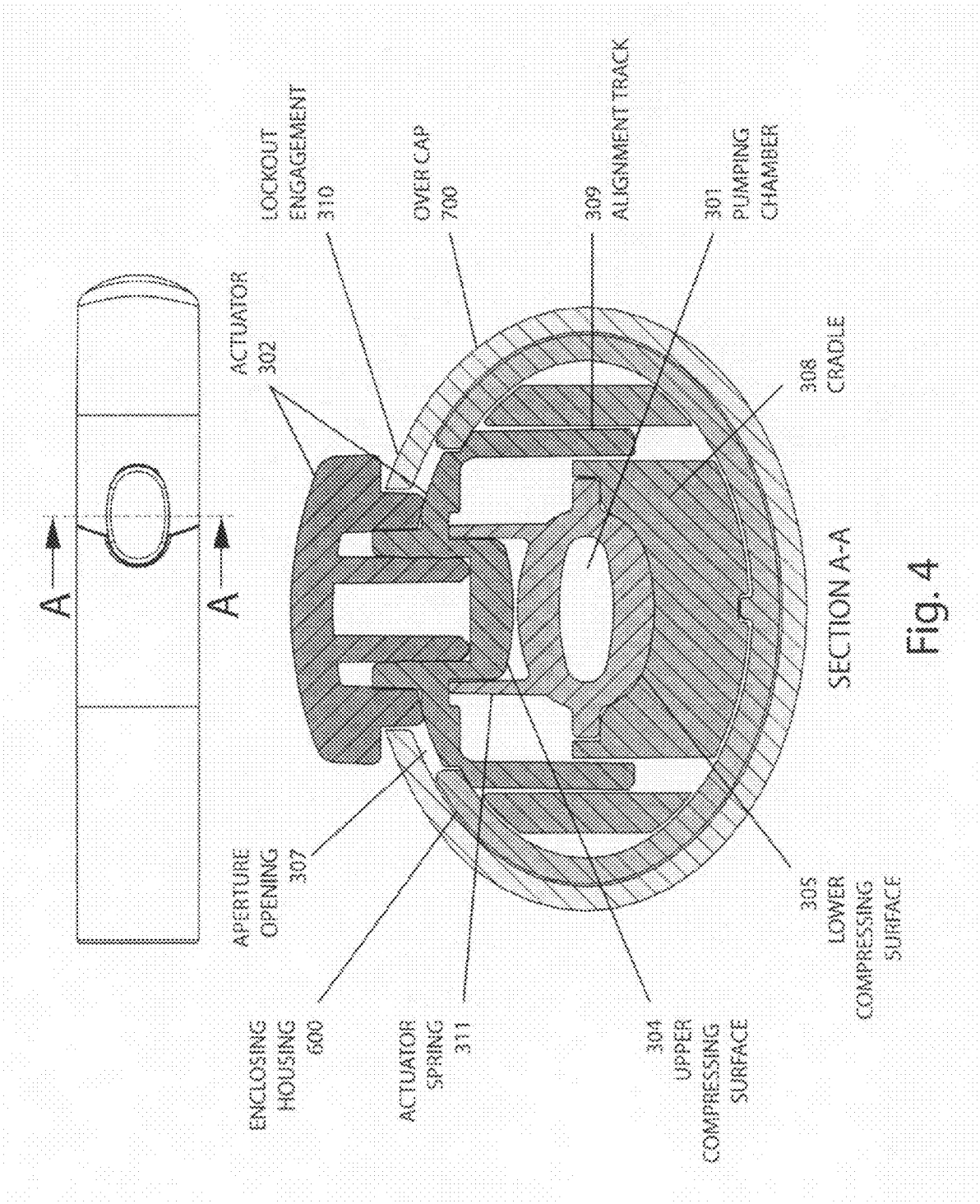
FIG. 4 is a cross-sectional view along the line A-A through an exemplary dispensing pump and finger depressible actuator according to an exemplary embodiment of the present invention, shown in its static or home state.

The operation of pumping chamber 301 is next described in greater detail. Continuing with reference to FIG. 3, in exemplary embodiments of the present invention pumping chamber 301 can, for example, be manually actuated by an actuator 302. Actuator 302 can, for example, be ergonomically configured, and can, for example, be configured as a button, a paddle or as a button appearing feature on a paddle. With reference to FIG. 4, actuator 302 can, for example, be physically contained in an aperture opening 307 through enclosing housing 600. Actuator 302 can, for example, be a single component or an assemblage of components (shown in FIGS. 3 and 4, for example, as a two-part subassembly) and can, for example, be caused to move in a controlled linear direction upon the pumping chamber by guidance provided by actuator alignment track 309.

Figure 15A:
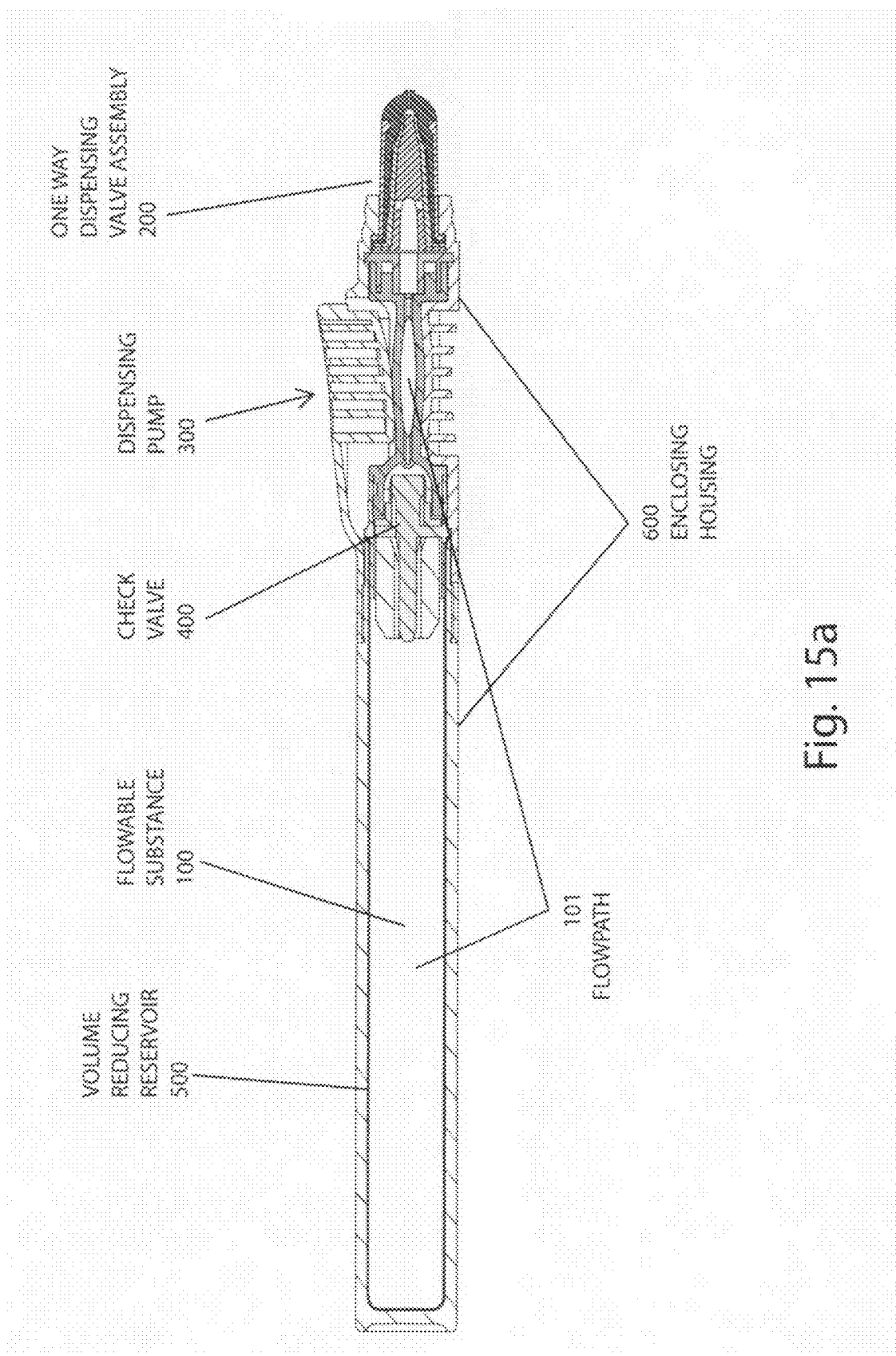
FIGS. 15a and 15b depict an alternate exemplary embodiment of the present invention from that depicted in FIGS. 1-3.
Figure 15B:
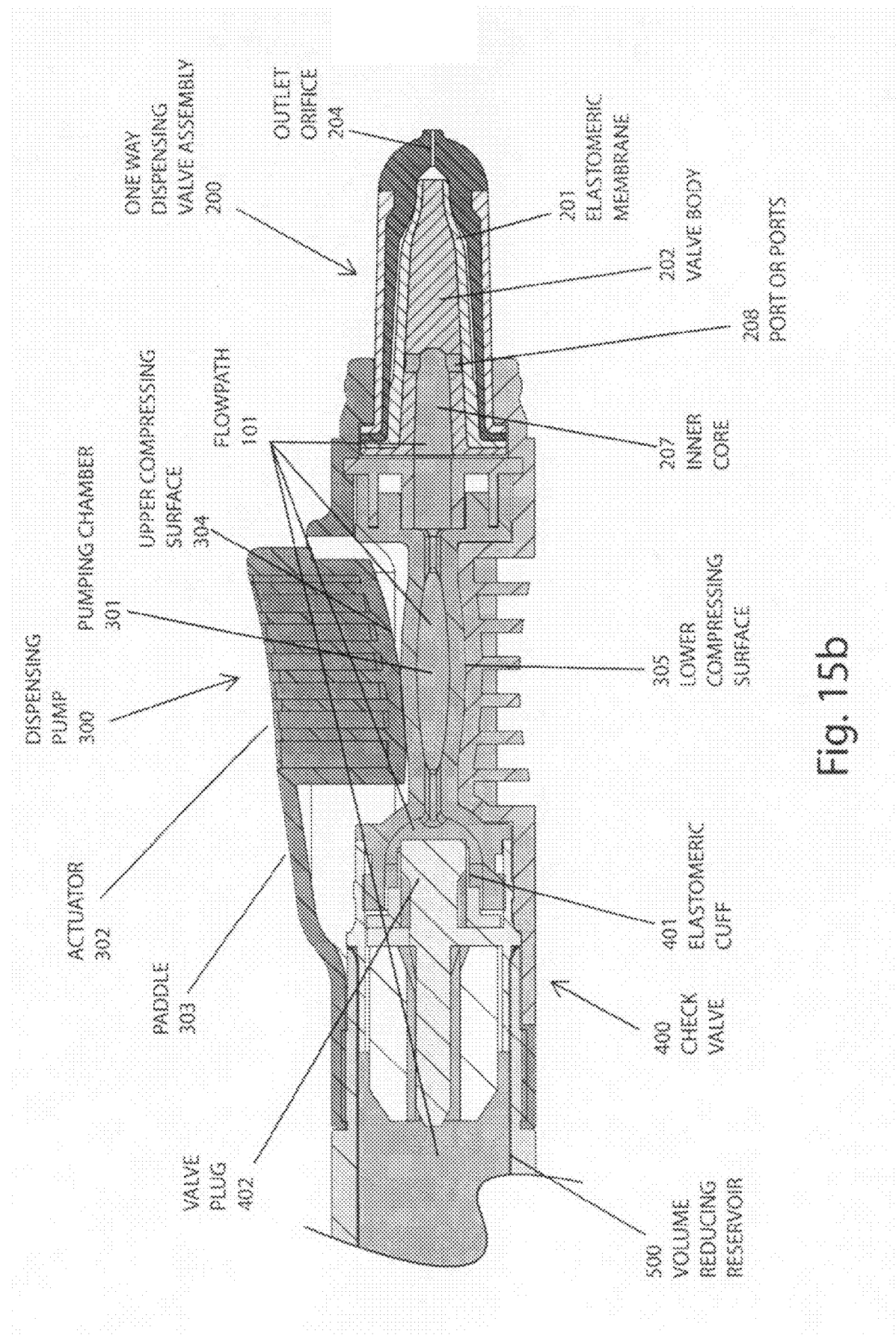

Alternatively, actuator 302 can, for example, as shown in FIGS. 15a and 15b, be integrally molded as a hinged extension of enclosing housing 600. Actuator 302 can, for example, provide a 1:1 force upon pumping chamber 301, or can, for example, be configured as an extended overhanging paddle 303 with finger activation contact being further from the paddle fixation than is the actuator to provide a mechanical advantage, such as, for example, 2:1. Alternatively, pumping chamber 301 can, for example, be configured with integrally formed features so as to be directly acted upon by a user's finger.

Additionally, for example, pumping chamber 301 can be sized to provide further mechanical advantage utilizing the known relationship of Force=Pressure×Area (F=PA). For example, the amount of force required to be applied upon pumping chamber 301 to effectively push any given volume, at a given viscosity, of flowable substance 100 through one way dispensing valve assembly 200 can be reduced by minimizing the compressible surface area of pumping chamber 301 while correspondingly increasing its overall stroke. Similarly, for example, the amount of pressure available to push flowable substance 100 through one way dispensing valve assembly 200 can, for example, be increased without requiring additional applied force, such as, for example, by minimizing the compressible surface area of pumping chamber 301.

Again with reference to FIG. 4, pumping chamber 301 is shown in a configuration prior to being compressed. Actuator spring 311, shown in section, can be, for example, an integrally molded compliant tubular feature protruding from elastomeric pumping chamber 301, and positioned to hold actuator 302 in a home (non-dispensing) position that does not compress pumping chamber 301 at all. Actuator spring's 311 function can, alternatively, be achieved in various other ways such as, for example, by using a separate elastomeric or mechanical spring or other resilient means, or, for example, by a flexible member extending from actuator 302 itself, or from other adjacent components. Alternatively still, the resilience of pumping chamber 301 itself may be sufficient to return the actuator 302 to its static position following each actuation. Such a resilient compressible pumping chamber can, for example, be molded with a low density polyethylene (LDPE) or thermoplastic elastomer (TPE), or, for example, silicone.

Figure 5:
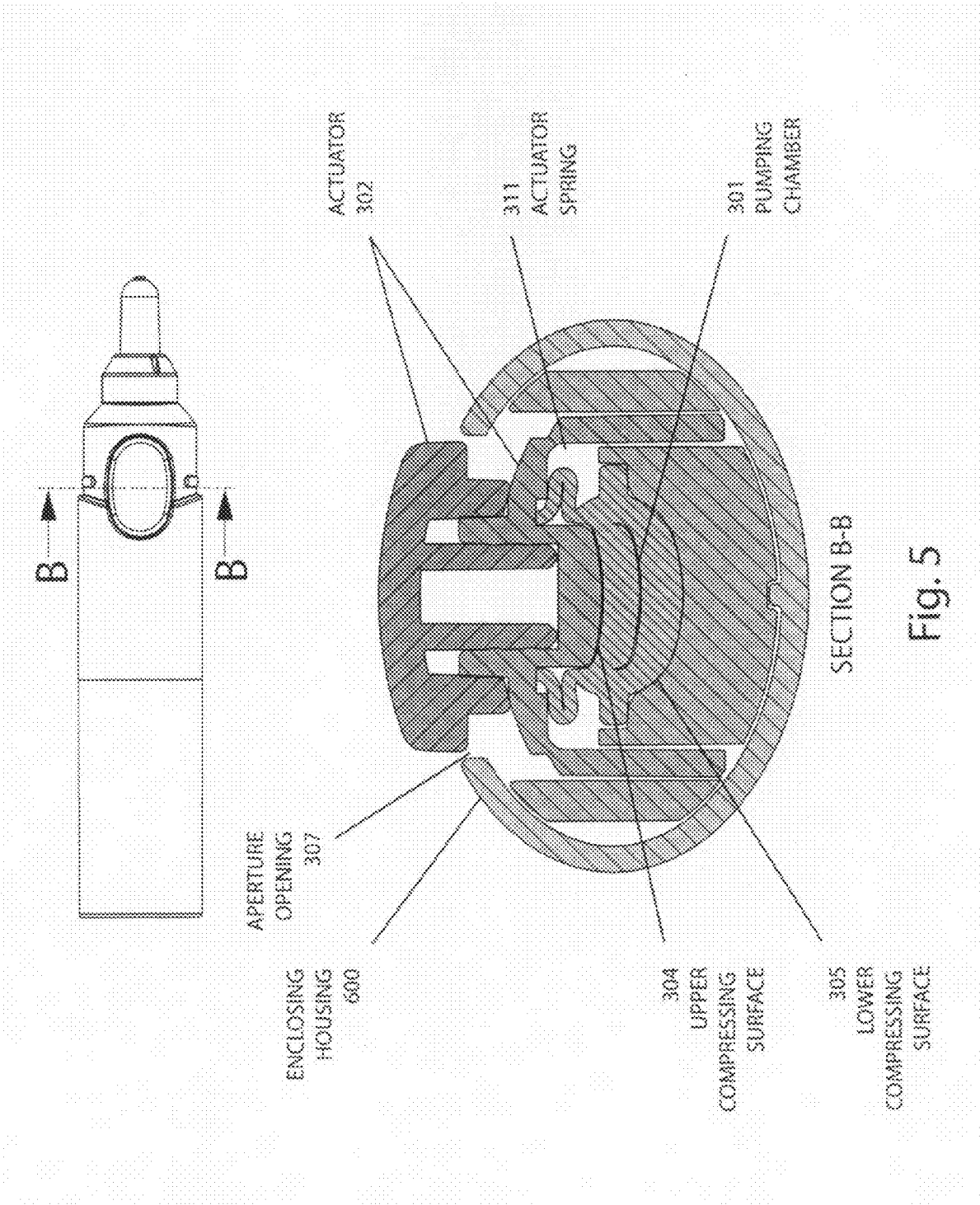
FIG. 5 is a cross-sectional view along the line B-B (essentially the same location as line A-A in FIG. 4) through the exemplary dispensing pump and finger depressible actuator of FIG. 4 shown with the pump in its actuated state.

Depressing actuator 302, for example manually, can cause actuator spring 311 to collapse, as shown, for example in FIG. 5, thus enabling pumping chamber 301 to be, for example, compressed between upper compressing surface 304 of actuator 302 and an opposing lower compressing surface 305. Lower compressing surface 305 can, for example, be integrally formed within enclosing housing 600 (as shown in FIGS. 15a and 15b) or can, for example, be integrally formed within a separate sub-assembled cradle 308 component used to support pumping chamber 301 (as shown in FIGS. 3-5).

FIG. 5 depicts pumping chamber 301 in its compressed or actuated state. With reference thereto, in exemplary embodiments of the present invention the contours of these opposing surfaces can, for example, generally be matched to provide intimate contact between such "upper" and "lower" surfaces (actually, they are semi-elliptical in the depicted example) during actuation so as to precisely control and maximize the volume of flowable substance 100 expelled from pumping chamber 301.

Alternatively, pumping chamber 301 need not be elastomeric but, rather, can, for example, use a piston or other mechanical type mechanism to pull a specific volume of flowable substance 100 out through check valve 400 into pumping chamber 301 and subsequently, to push that volume of flowable substance 100 through one way dispensing valve assembly 200. Such a piston, can, for example, be manually actuated by an ergonomically configured finger depressible actuator 302, as shown, for example, in FIGS. 3-5.

As noted above, in alternate exemplary embodiments of the present invention, pumping chamber 301 can, for example, use a piston, diaphragm, concertina or other mechanical type mechanism to displace a specific volume of flowable substance 100 out through check valve 400 into pumping chamber 301. In such alternate exemplary embodiments the volume expelled from pumping chamber 301 can be precisely controlled by specifying the beginning and ending stroke positions of such mechanism.

Returning now to FIG. 3, sealed flowpath 101 between one way dispensing valve assembly 200 and check valve 400 can be substantially non-expandable or, where flexible, can be confined within the surfaces of enclosing housing 600, thus creating a physically restricted displacement such that activation of dispensing pump 300 causes a volume equal to substantially all of the flowable substance 100 driven from pumping chamber 301 to be pushed through and expelled from one way dispensing valve assembly 200 (it is noted that there is a small residual volume of flowable substance 100 that remains in the inner core of the valve, but whatever volume is pushed out of the pumping chamber is in fact expelled from the valve outlet orifice; it is just that some of that volume comes from the valve's inner core, and some of what leaves the pumping chamber then remains in the valve's inner core after each dose).

Figure 6:
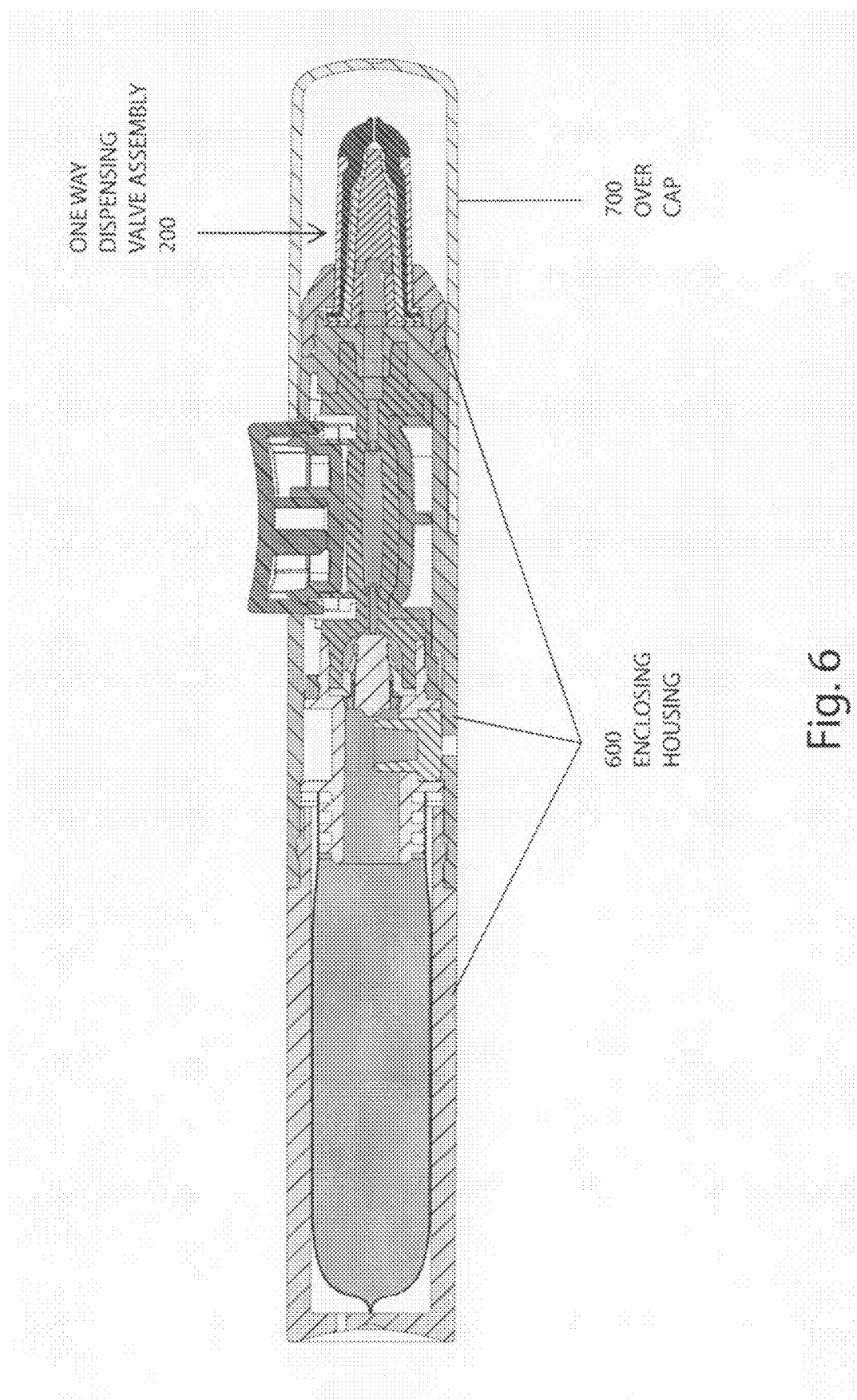
FIG. 6 is a longitudinal cross sectional view showing the overall assembly with an exemplary enclosing housing.

FIG. 6 shows the exemplary delivery system of FIGS. 1-3 with removable over cap 700 attached onto enclosing housing 600 so as to cover one way dispensing valve assembly 200. This can be done, for example, when the delivery system is not in use to protect one way dispensing valve assembly 200 from physical or ambient contaminants. In exemplary embodiments of the present invention, removable over cap 700 can be treated, embedded or coated with anti-microbial ingredients. Removable over cap 700 can also, as shown in FIG. 4, include a lockout engagement 310 which can, for example, prevent actuator 302 from being depressed when the device has the over cap 700 attached to it. This works, for example, by an edge of over cap 700 pass underneath an overhanging feature or features provided on actuator 302 when over cap 700 is fastened to the device.

FIG. 7 depict various views of an exemplary terminating outlet orifice according to exemplary embodiments of the present invention. As noted, the delivery or dispensing of flowable pure or sterile substance 100 in controlled metered volumes, such as, for example, as little as 20 microliters or, for example, as large as 50 microliters, is desired for many nutraceutical, cosmeceutical or pharmaceutical products, such as, for example, eye care solutions. Larger volumes can be similarly dosed by modifying the dimensionality of pumping chamber 301 (FIGS. 3-5). With reference to FIG. 7, in exemplary embodiments of the present invention, in order to effectively control the volume of expelled flowable substance 100, one way dispensing valve assembly 200 can, for example, be provided with a nipple feature 203 that protrudes beyond surrounding adjacent surfaces. Nipple feature 203 can, for example, comprise an outlet orifice 204, through which flowable substance 100 can be expelled, together with a terminating surface feature 205.

In exemplary embodiments of the present invention, outlet orifice 204 can, for example, be an aperture or hole, and can, for example, be sized for optimal expulsion of a desired volume of flowable substance 100. The outlet orifice 204 can, for example be a pin pierced hole through a flexible thermoplastic elastomer such that the orifice is normally closed and only expands when pressure is applied to the flowable substance. Outlet orifice 204 can also, for example, be molded to be as small as is then cost effective to produce, such as, for example, to 0.008" diameter. Terminating surface feature 205, through which outlet orifice 204 exits, can, for example, be adjacent to and co-axially surround outlet orifice 204, and can, for example, extend or protrude away from surrounding surfaces. Additionally, terminating surface feature 205 can, for example, have a distinct edge and minimal surface area, and can be made, for example, with hydrophobic materials so as to minimize surface tension so as to thus freely release an expelled volume of flowable substance 100 from outlet orifice 204 as a stream, small droplet or series of small droplets, with minimal or no residual amount remaining adhered to nipple feature 203. It is noted that preventing or limiting any residual amount of expelled flowable substance 100 from remaining adhered to valve tip 211 (see FIG. 7b) can, for example, be important to insure that a maximum portion of the dispensed amount of flowable substance 100 is delivered to the desired target when delivering small volumes such as a single drop.

FIG. 7c depicts an alternate exemplary embodiment, where no nipple feature is used, and thus outlet orifice 204 simply exits from the surface of valve tip 211 itself. Such an embodiment can be used, for example, when dispensing fluid in a stream.

Various details of one way dispensing valve assembly 200 will next be described with reference to FIGS. 8-10. It is noted that one way dispensing valve assembly 200 can be, for example, any type of one way valve. For example, the valves of this type described in U.S. Pat. No. 7,513,396, issued on Apr. 7, 2009, or U.S. Published Patent Application No. 2009023634, published on Sep. 24, 2009, or various modifications thereof, can be used. Alternatively, any other type of one way valve can be used, such as, for example, a duck-bill valve, disk valve, ball valve, umbrella valve, etc.

With reference to FIG. 8a, in exemplary embodiments of the present invention valve body 202 can be made, for example, from a rigid plastic (for example, high density polypropylene) and can, for example, have flowpath 101 extend axially from dispensing pump 300 through an inner core 207 of valve body 202. Valve body 202 can have, for example, at least one port 208 which extends flowpath 101 transversely through valve body 202 from inner core 207 to an outer surface of valve body 202. It is noted that in exemplary embodiments of the present invention such as are depicted in FIG. 8a, flowpath 101 through inner core 207 can extend distally somewhat beyond ports 208. Such a configuration can be used to facilitate generally consistent wall part thickness in manufacturing so as to minimize exterior surface flaws resulting from sink, i.e., shrinkage of the plastic during cooling of thicker sections following injection molding.

Alternatively, with reference to FIG. 8b, flowpath 101 can, for example, be truncated, stopping at the distal side of port(s) 208. The function of such a truncated inner core 207 is to avoid dead-end void volumes which might otherwise entrap air, which can cause reciprocity issues whereby any such entrapped air could compress and decompress during pump actuation, reducing the effectiveness of the pump. In either configuration (i.e., that of FIG. 8a or 8b), the entire fluid flowpath 101 should best remain purged of air volumes at all times to prevent or minimize potential reciprocity issues.

In exemplary embodiments of the present invention, an elastomeric membrane 201 can be tightly fitted over the outer surface of valve body 202 so as to create a constricted temporary passageway (also referred to below as a "temporary restricted space" 218-FIG. 9) for flowable substance 100 from port(s) 208 to outlet orifice 204, while at the same time preventing any backflow into any residual pure or sterile substance 100 contained within the sealed delivery system. When at rest, elastomeric membrane 201 can be tightly compressed upon the outer surface of valve body 202 (and thus the openings of ports 208 as well), thus completely sealing off outward flow as well as inward contamination. In exemplary embodiments of the present invention, these mating surfaces (i.e., elastomeric membrane 201 and the outer surface of valve body 202) should be sufficiently smooth so as to prevent the possibility of allowing for microbial pathways.

Thus, elastomeric membrane 201 can, for example, be assembled onto valve body 202, or can, for example, be over-molded directly onto valve body 202 using, for example, a non-bonding separable polymer with molding shrinkage to achieve a tight and intimate shrink fit as the elastomer membrane 201 shrinks upon the outer surface of valve body 202.

In exemplary embodiments of the present invention, the tightness of the fit of elastomeric membrane 201 over the outer surface of valve body 202 can be made significantly high so as to insure proper resealing, while at the same time not be so high so as to make it impractically difficult for a user (who may typically be elderly, young, injured, or otherwise weakened, depending upon the flowable substance 100 being dispensed) to push flowable substance 100 through port(s) 208 and out through the said constricted temporary passageway between elastomeric membrane 201 and the outer surface of valve body 202. For example, the elastomeric membrane 201 can preferably be made to fit relatively tightly over the valve body 202 for dispensing viscous flowable substances 100 such as, for example, ointments or creams, or relatively less tightly for dispensing individual droplets of aqueous fluids, such as eye drop solutions. The object being always to have the elastomer fit snugly enough but yet still be actuatable without significant effort by a user. In exemplary embodiments of the present invention such tight fits can be created by using interference percentages of between, for example, 2% and 10%.

In exemplary embodiments of the present invention, as shown for example in FIG. 8b, one way dispensing valve assembly 200, valve cover 209, inner elastomeric layer 210, elastomeric membrane 201, and inner core 207 can, for example, each terminate proximally (bottom of figure) with a radially outwardly extending flange 212. Such flange in 3D appears as a ring extending from the outer diameter of each of such structures (as shown in FIG. 11e). The multiple layers comprising the outwardly extending flange 212 can, for example, each be intimately fitted together, with flange 212 assembled under compression, for example, by a retaining collar 601 (as shown in FIG. 3) which can affix the flange 212 to enclosing housing 600 via, for example, a threaded engagement or a press fit 504 or a one-way barbed snap fit, to thus seal and extend flowpath 101 extending from dispensing pump 300 into one way dispensing, valve assembly 200.

FIG. 8c is a longitudinal cross-sectional isometric view of the valve cover and inner elastomeric layer of the continuously sealing one way dispensing valve assembly of FIGS. 8a and 8b showing detail of the spacer ribs 217 which extend inwards from the valve cover 209 through the inner elastomeric layer 210. These are described more fully below.

Figure 9:
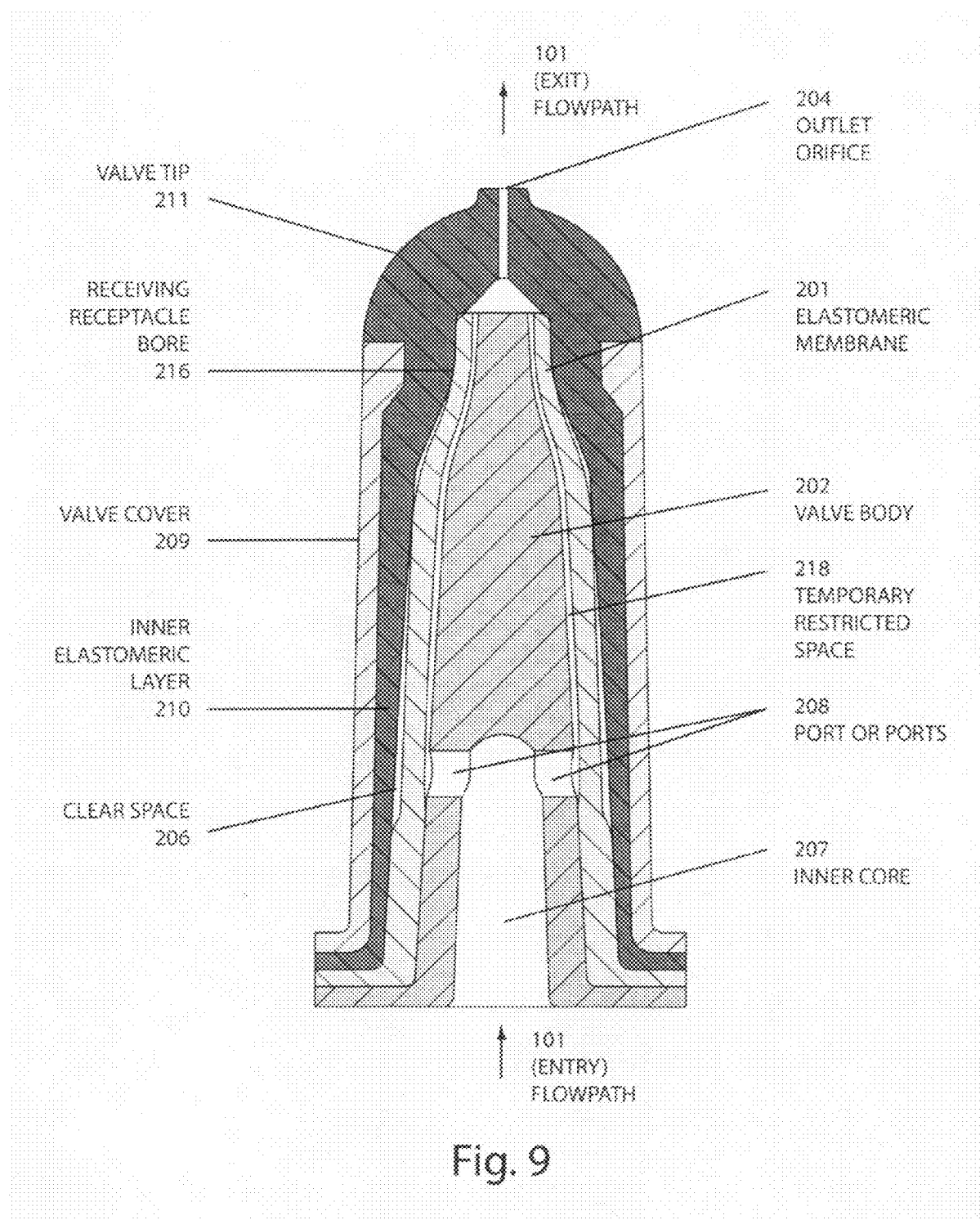
FIG. 9 is an exemplary view of the continuously sealing one way dispensing valve assembly of FIG. 8b shown with the valve in dispensing position.

FIG. 9 depicts the exemplary valve assembly of FIG. 8 in a dispensing position. Thus, with reference to FIG. 9, a temporary restricted space 218 is seen, thus extending flowpath 101 between the inner surface of displaceable flexible elastomeric membrane 201 and the outer surface of valve body 202. As a result, flowable substance 100 can pass through this temporary constricted space, created by positive pressure upon flowable substance 100 as a result of a user actuating dispensing pump 300, as described above.

Figure 11B:
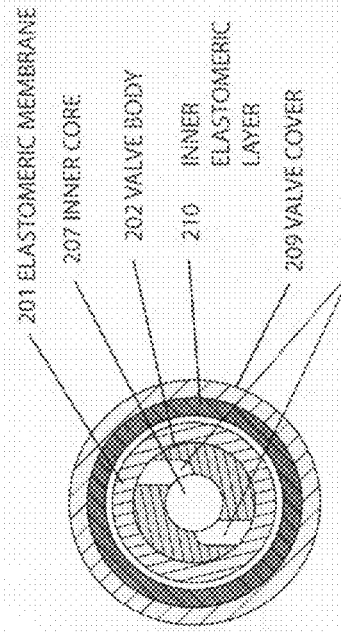
FIGS. 11a-11c are axial cross sectional views though various exemplary port configurations in a one way dispensing valve assembly according to various alternative exemplary embodiments of the present invention.
Figure 11D:
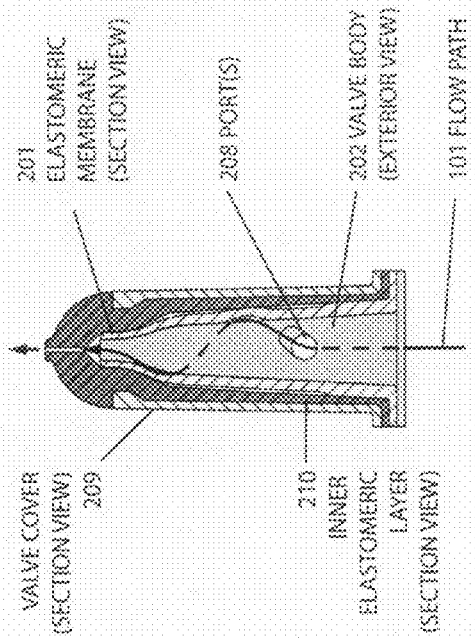
FIG. 11d is a longitudinal partial cross sectional view through a one way dispensing valve assembly according to an exemplary embodiment of the present invention showing another alternative port(s) configurations.
Figure 11A:
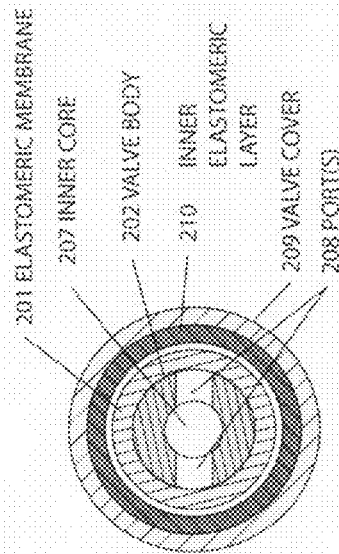
Figure 11C:
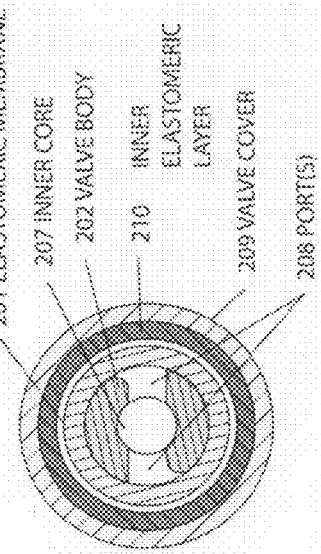

FIG. 9 also depicts ports 208. These can be implemented in a variety of ways. Thus, FIGS. 11a, 11b, 11c and 11d respectively depict various alternative exemplary embodiments of port(s) 208 that can, for example, be used. For example, port(s) 208 can be perpendicular to the central axis of valve body 202 as shown in FIG. 11a. Alternatively, as shown in FIG. 11b, port(s) 208 can, for example, be angularly skewed relative to the central axis of valve body 202, or as shown in FIG. 11c, the distal end of port(s) 208 can, for example, be formed with an inclined sloping edge, so as to help direct flowable substance 100 between elastomeric membrane 201 and valve body 202 with less pressure. Further, as shown in partial cutaway sectional view FIG. 11d, the angulation or form of port(s) 208 can, for example, be articulated so as to direct flowable substance 100 in a helical manner from port(s) 208 towards outlet orifice 204, so as to flow more efficiently. Finally, for example, the positioning of port(s) 208 can be staggered along the central axis of valve body 202 so as to control the direction of flow of flowable substance 100 from port(s) 208 to outlet orifice 204.

Returning to FIG. 9, in exemplary embodiments of the present invention, a valve cover 209, preferably made with rigid plastic (for example, high density polypropylene), can, for example, encircle and protect elastomeric membrane 201 from external influences. Valve cover 209 can, for example, be spaced radially outward, away from the outer surface of elastomeric membrane 201, and can have, for example, an inner layer 210 of elastomeric material extending axially to and beyond the outlet end of valve body 202 and elastomeric membrane 201. The elastomeric material of said inner elastomeric layer 210 can, for example, form a soft elastomeric valve tip 211 of increased thickness over the outlet end of one way dispensing valve assembly 200, which can be particularly advantageous when the valve assembly is used for dispensing an eye care solution, for example. This is because such a soft elastomeric valve tip 211 can, for example, prevent potential damage should it inadvertently make contact with an eye.

Inner elastomeric layer 210 and valve tip 211, can, as shown in FIG. 8c, be integrally adjoined and become a part of valve cover 209 by first molding plastic valve cover 209 and then two shot molding or overmolding 505 the elastomeric inner layer 210 and valve tip 211 features onto valve cover 209. It is commonly understood in the injection molding industry that when overmolding a plastic part, it is common to intentionally have the molded part remain captured within, for example, the A side of the mold when the mold opens, and to then substitute a (second) alternate B side of the mold to facilitate overmolding a second material onto the first. The inclusion of molded spacer rib 217 features on the (inside of) the valve cover 209 can, for example, enable valve cover 209 to be spaced away from the (second) alternate B side of the mold, thereby controlling the position of valve cover 209 within the closed mold when overmolding the inner elastomeric layer 210.

Returning again to FIG. 9, in exemplary embodiments of the present invention a clear space 206 can be provided between elastomeric membrane 201 and inner elastomeric layer 210. Clear space 206 can have, for example, a controlled clearance so as to limit the expansion of elastomeric membrane 201 when a metered volume of flowable substance 100 is dispensed through outlet orifice 204, as described above. It is noted that in exemplary embodiments of the present invention the material forming outlet orifice 204 can, for example, be arranged or formulated so as to not absorb flowable substance 100. Additionally, as noted, the constriction of elastomeric membrane 201 upon the outer surfaces of the valve body 202 immediately reseals the temporary extension of flowpath 101 upon cessation of positive pressure upon flowable substance 100. Thus, any flowable substance 100 entering outlet orifice 204 can be ejected and cannot return into the temporary space between the inner surface of elastomeric membrane 201 and the outer surface of valve body 202.

In exemplary embodiments of the present invention, as shown in FIG. 9, the distal surfaces of elastomeric membrane 201, through which flowable substance 100 exits, can be arranged so as to be in intimate physical contact with the inner surface of the elastomeric valve tip 211, thus confining and directing the entirety of flowable substance 100 through outlet orifice 204. In this context the term "intimate physical contact" is understood to include surfaces that either touch or have an interference fit; thus, for example, the external surfaces at the distal end of elastomeric membrane 201 can have an intimate male/female mating fit within a receiving receptacle bore 216 provided in the inner portion of elastomeric valve tip 211. Given such a configuration, all flowable substance 100 exiting the elastomeric valve tip can be directed to, and be ejected from, outlet orifice 204 and thus cannot divert into clear space 206. The interoperability of clear space 206 and receiving receptacle bore 216 at the same time allows the creation of temporary restricted space 218 with a reasonable amount of pressure applied to the flowable substance, and yet at the same time insures that such flowable substance cannot "spill over" into said clear space 206 upon ejection.

In exemplary embodiments of the present invention, the thickness of elastomeric membrane 201 need not be uniform. The membrane wall can, for example, as shown in FIGS. 8 and 9, become progressively thinner at the distal end, or, for example, as shown in FIG. 10, become progressively thicker at the distal end, in various exemplary embodiments. This is due to the fact that some flowable substances 100 are best dispensed, and the valve assembly best resealed, where the thickness of the elastomeric membrane increases distally; in other contexts, an exemplary valve assembly operates best where the thickness of elastomeric membrane 201 decreases distally. In general, this feature will be a function of the inner pressures created in the pump and valve, the viscosity and density of the flowable substance 100, the size of the pumping chamber and the related desired size of dispensed metered amount of flowable substance 100, and is thus a design and application dependent parameter.

With reference to FIG. 12a, clear space 206 can, for example, have one or more vent openings 213, said vent opening(s) 213 passing as a channel or channels extending radially outward between the compressed mating flanges 212 of elastomeric membrane 201 and the adjacent inner elastomeric layer 210. Such vent opening or openings 213 can, for example, ensure that clear space 206 does not experience an increase or decrease in pressure as elastomeric membrane 201 expands and constricts. It is noted that such an uncontrolled underpressure in clear space 206, at a time when flowable substance 100 is being ejected towards outlet orifice 204, could cause flowable substance 100 to be sucked into clear space 206 and thus be diverted away from being ejected through outlet orifice 204, an obviously undesirable occurrence.

Alternatively, as shown in FIG. 12b, one or more vent openings 213 can pass through the walls of valve cover 209 and its inner elastomeric layer 210, allowing clear space 206 to communicate with ambient outside space. It is noted that the exemplary implementation of vents 213 as shown in FIG. 12a is easier to mold, as such vents can be molded without mold side action, as opposed to the implementation of vents 213 depicted in FIG. 12b which require molding with side action in the molding tool.

Returning for a moment to FIGS. 7a and 7b, it is noted that when flowable substance 100 passes from the temporary restricted space 218 it communicates through outlet channel 215 to be expelled from outlet orifice 204. Outlet channel 215 and outlet orifice 204 can, for example, as shown in FIG. 7a comprise a narrow constricted path such as a pinhole of small diameter such as, for example, 0.007"-0.020", such as is used as the diameter of a fine hypodermic syringe needle. Using such an outlet channel, if one squeezes quickly a stream is dispensed, but if the flowable substance is more slowly expelled, then a drop or series of drops will result, as described below.

Figure 13A:
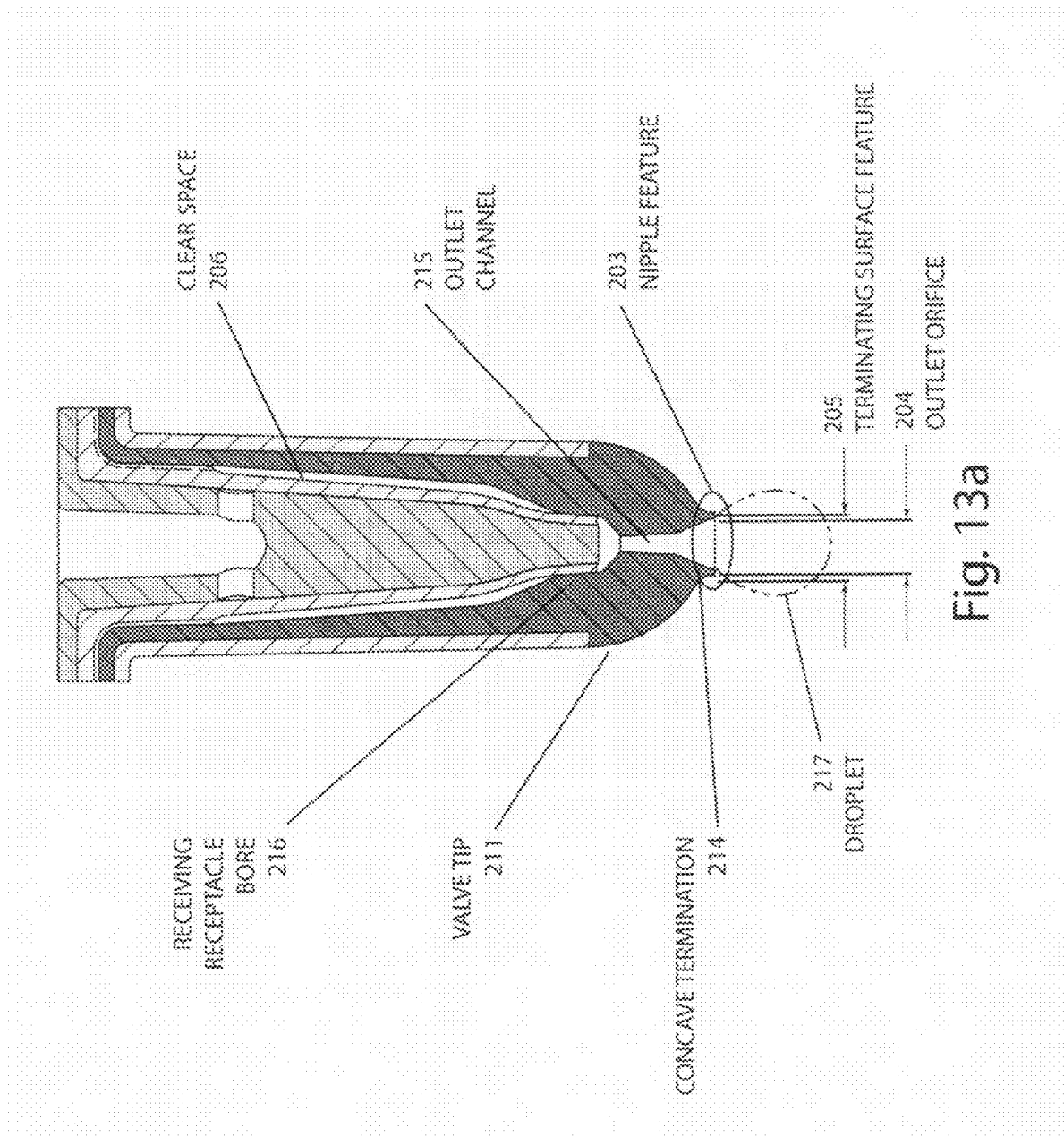
FIGS. 13a-13b are exemplary views of the continuously sealing one way dispensing valve assembly of FIG. 12a with alternative nipple and outlet orifice feature details (valve assembly shown in dispensing orientation)

It is further noted that the details of valve tip 211, outlet orifice 204, nipple feature 203, and terminating surface feature 205, can, for example, alternatively be configured in various other ways so as to produce specific desired droplet sizes, as next described. For example, as shown in FIG. 13a, an exemplary outlet orifice 204 can be provided with a concave termination 214, specifically sized and shaped to achieve an appropriate surface tension relative to the viscosity and density of flowable substance 100, so as to hold an exemplary droplet 217 as it is being dispensed, until such droplet sufficiently increases in volume such that its weight overcomes its surface tension, thus enabling the droplet to self-release from valve tip 211. Concave termination 214 can, for example, be approximately 0.5 mm in diameter to controllably produce droplets of a desired volume of, for example, 20 to 30 microliters. Alternatively, concave termination 214, as shown for example in FIG. 13b, can be larger, such as, for example, approximately 1.0 mm in diameter, to controllably produce larger droplets, such as, for example, of 40 to 50 microliters.

Figure 13B:
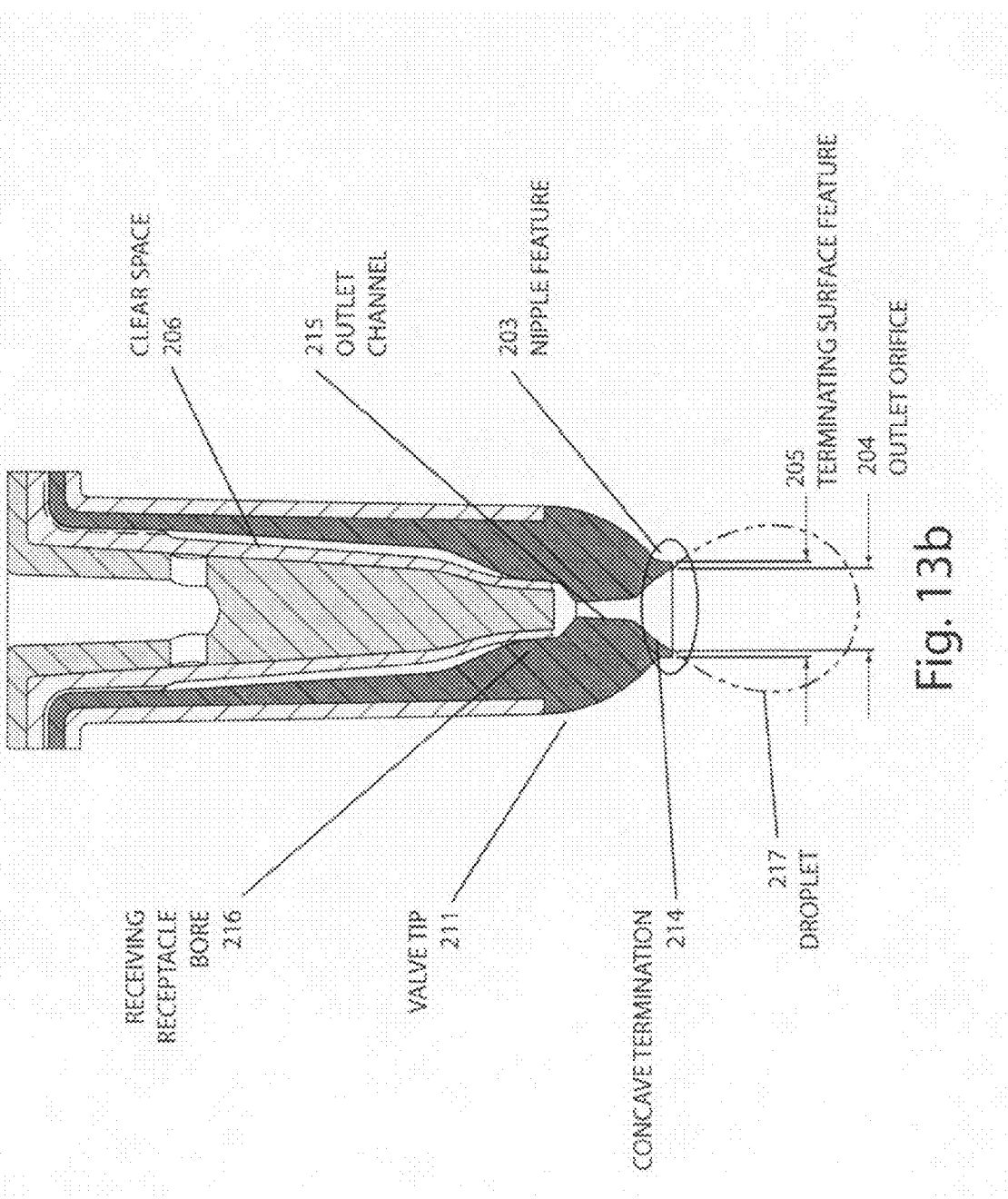

Continuing with reference to FIGS. 13a and 13b, outlet channel 215 can communicate through a concave termination 214 to outlet orifice 204. Outlet channel 215 can be tapered over its length, from a narrow restrictive proximal entrance aperture to a larger distal exiting aperture (adjacent to concave termination 214), so as to slow the velocity of flowable substance 100 passing through it. As is known, the velocity of a fluid decreases as the diameter of a channel through which it passes increases. Therefore, an outlet channel 215 which increases in sectional area toward its distal end can effectively reduce the velocity of expelled flowable substance 100 from a stream to the controlled dispensing of individual droplets. In some exemplary embodiments of the present invention, outlet channel 215 can be, for example, 0.015" in diameter at its narrowest (proximal) point and increase in diameter to, for example, 0.030" in diameter at its widest (distal) point. Such exemplary embodiments can also include a protruding nipple feature 203 and a sharp edged terminating surface feature 205, to provide additional control of the size and volume of individual dispensed droplets, as described above with reference to FIGS. 7a and 7b.

Figures 13C, 13D:
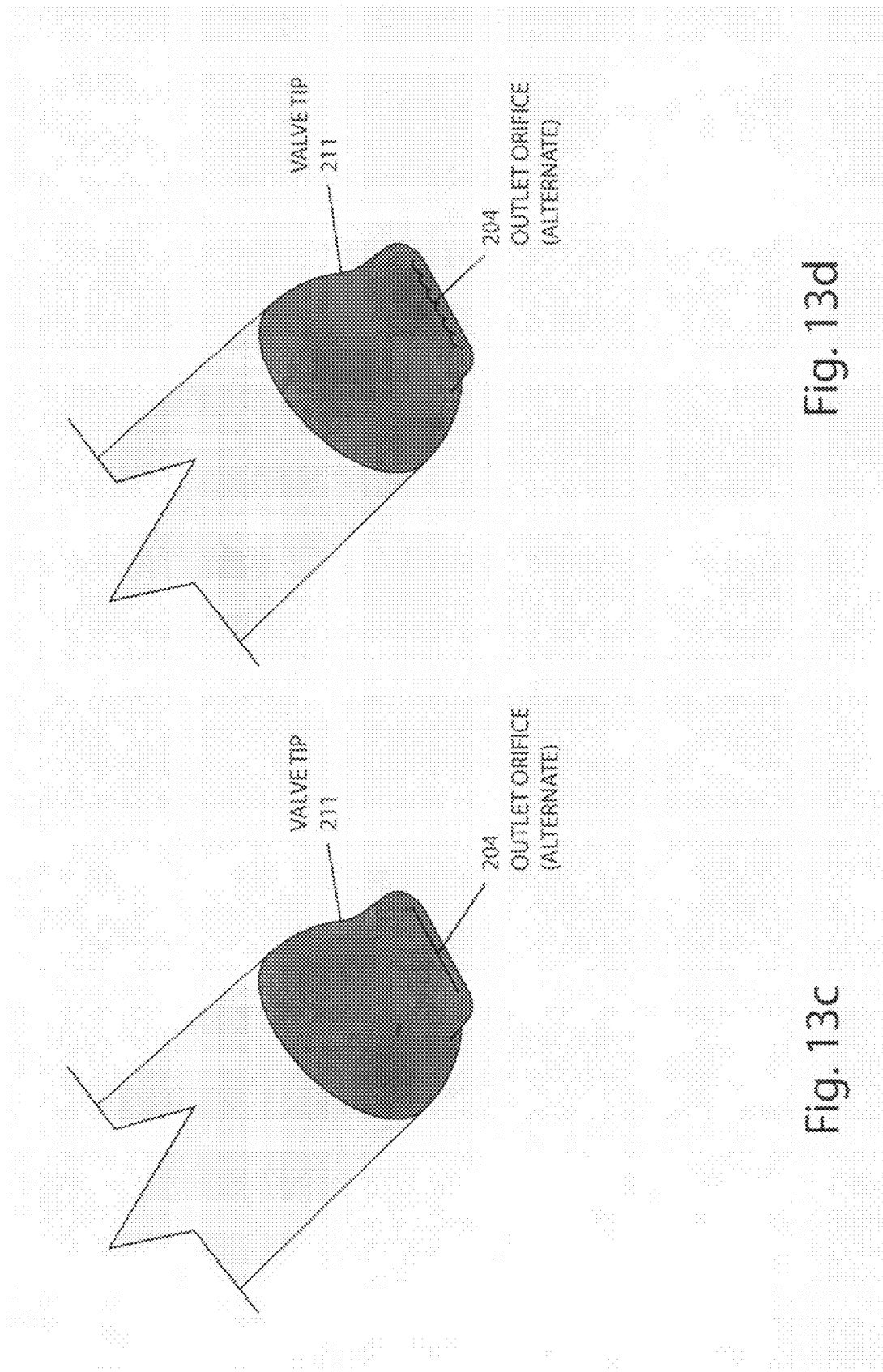
FIGS. 13c-13d are exemplary views of variant outlet orifices used to achieve spray mist and ribbon like discharges.

Continuing with reference to FIGS. 13c and 13d, valve tip 211 can also have, for example, a slotted outlet orifice 204, which can be useful to expel, for example, thicker fluid substances, such as gels or creams, in a ribbon like manner. Slotted type outlet orifice 204 can, for example, be produced by slitting a flexible thermoplastic elastomeric material such that the outlet orifice is normally closed and then spreads to open when pressure is applied upon flowable substance 100. Alternatively, as shown in FIG. 13d, valve tip 211 can, for example, have an outlet orifice 204 comprised of a linear array of interconnected semi-circular slits, which can be useful, for example, to expel solutions in a mist. It is noted that the configurations of FIGS. 13c and 13d can, for example, be designed, in exemplary embodiments of the present invention, so that the distal flattened portion (essentially a duckbill shape) comprises approximately ⅓ of the overall valve tip. Moreover, the flat incision of FIG. 13c, or the set of hemispherical incisions of FIG. 13d, should extend form the tip of the valve down to where the outlet channel begins in, for example, FIG. 13a, such that instead of a small cylindrical outlet channel traversing the distance between the distal end of the valve cover and the outlet orifice, instead an outlet slit is used. When a flowable substance under pressure is expelled from the valve, it oscillates within such slit, much like air oscillating along the reed of a woodwind instrument (e.g., oboe), and a ribbon like discharge of the cream or viscous flowable substance results.

Figure 13E:
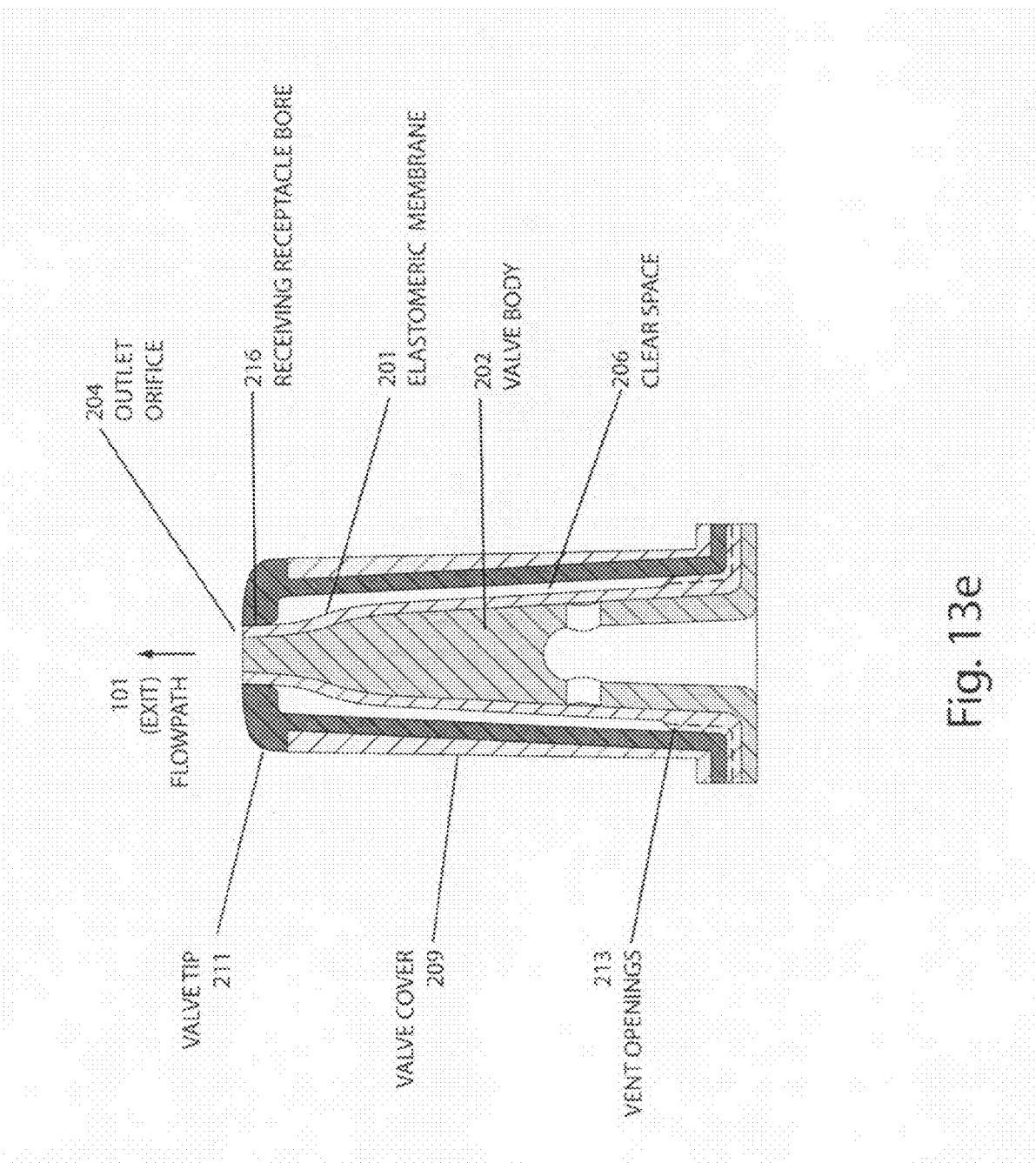
FIG. 13e is an exemplary view of a variant valve tip where the elastomeric membrane passes through the valve tip.

Alternatively, as shown, for example in FIG. 13e, elastomeric membrane 201 can, for example, extend completely through valve tip 211 (here shown provided with receiving receptacle bore 216) so as to expel flowable substance 100 directly from the temporary space 218 between valve body 202 and elastomeric membrane 201, rather than through a separate outlet channel 215 and outlet orifice 204. Additionally, for example, going one-step beyond that shown in FIG. 13e, elastomeric membrane 201 can, for example, extend even beyond through valve tip 211 to serve, as it were, as its own nipple.

It is noted that these exemplary alternative geometries for outlet orifice 204, outlet channel 215 and valve tip 211 are not intended to limit the present invention in any way, but rather are provided to indicate that one skilled in the art can readily adjust such geometries to achieve alternative desirable characteristics for any particular expelled flowable substance 100.

It is noted that whereas outlet orifice 204, as shown, for example, in FIGS. 7a and 7b, can be used to control the dispensing of flowable substance 100 as a fine liquid stream or small droplets, the exemplary outlet orifices as shown in FIGS. 13a and 13b are configured to control dispensing of specific drop sizes as previously described. Moreover, the less restrictive valve tip configurations as shown in FIGS. 13c, 13d and 13e can be used, for example, for dispensing more viscous substances such as, for example, creams or lotions, or for desired larger dispensing volumes, such as, for example, larger than 50 microliters. Such various alternative configurations are thus provided as examples, illustrating that the design of valve tip 211 and supporting structures can be specifically configured in any number of ways so as to facilitate alternative exiting flow characteristics as may be desirable or appropriate for dispensing particular flowable substances 100 relative to, for example, their inherent viscosity, desired dose volumes or desired application characteristics.

Figure 14A:
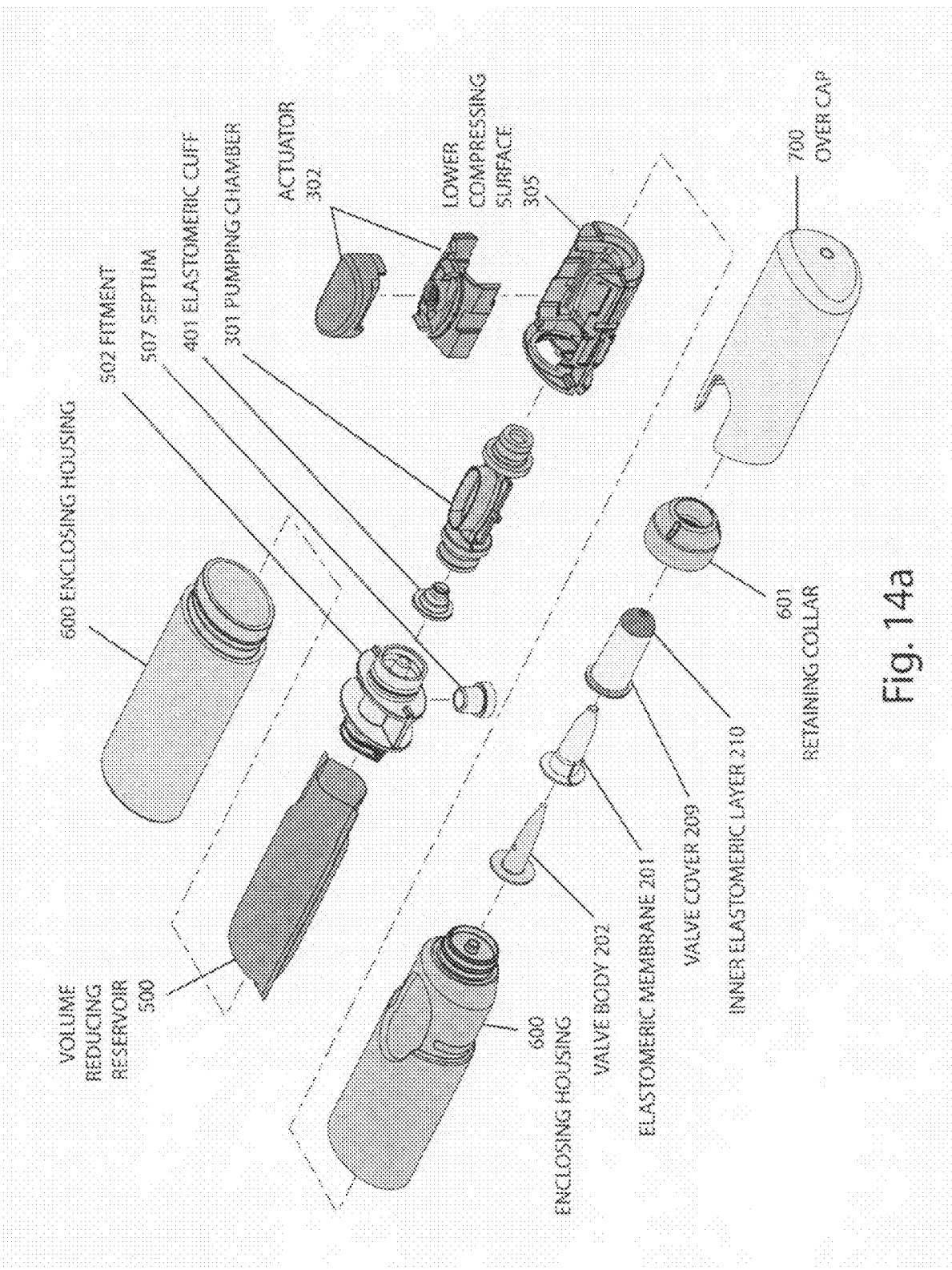
FIG. 14a is an exploded view of the exemplary system assembly of FIGS. 1-3.

FIG. 14a shows an exploded view of components as can be used to comprise an exemplary embodiment of a dispensing system according to an exemplary embodiment of the present invention as depicted in FIGS. 1-3, and FIGS. 14b and 14c show such a dispensing system as fully assembled, and broken into fully assembled subassemblies, respectively.

FIGS. 15a and 15b show an alternate exemplary embodiment of the dispensing system depicted in FIGS. 1-3. This alternate exemplary embodiment includes, for example, an integrally molded actuator 302 as a hinged extension of enclosing housing 600. By extending this extension to various lengths beyond the actuator 302, a mechanical advantage can be obtained, thus making it easier for, for example, weaker individuals, to push out standard viscosity substances in general, or compensating for substances with a high viscosity in particular, which can often be useful and will, in general, be a function of various factors such as, for example, average age of anticipated user, actual viscosity, frequency of use required for various flowable substances being dispensed, etc.

It is noted that one skilled in the art can easily envision alternative ways to configure and assemble the described functional elements to comprise a sealed fluid path within the delivery system, as well as an integrally formed or assembled enclosing housing 600 (as shown, for example, in FIGS. 15a and 15b).

Figure 16A:
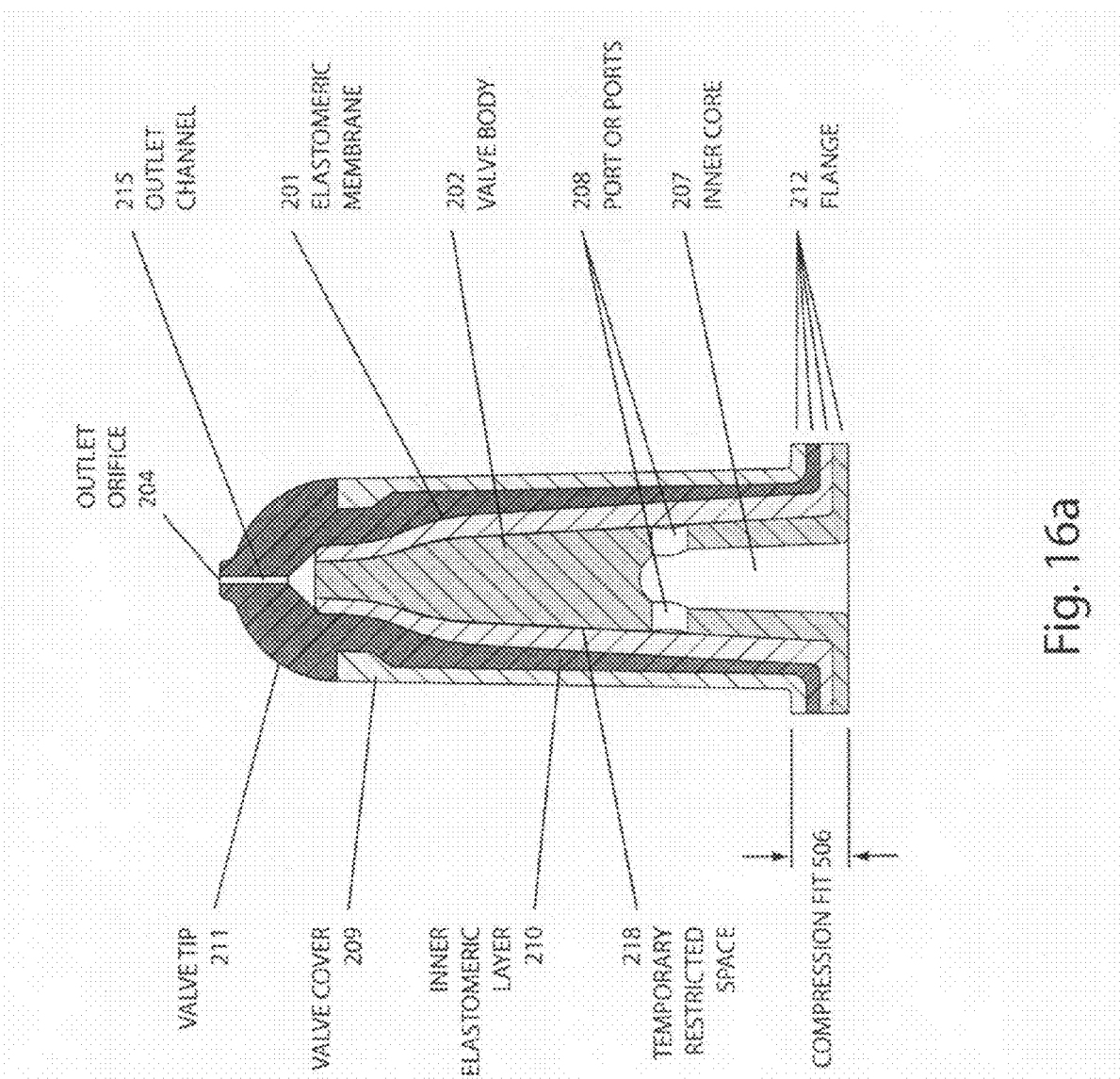
FIG. 16a depicts an alternate exemplary embodiment of the exemplary valve assembly depicted in FIG. 12a without a clear space.
Figure 16B:
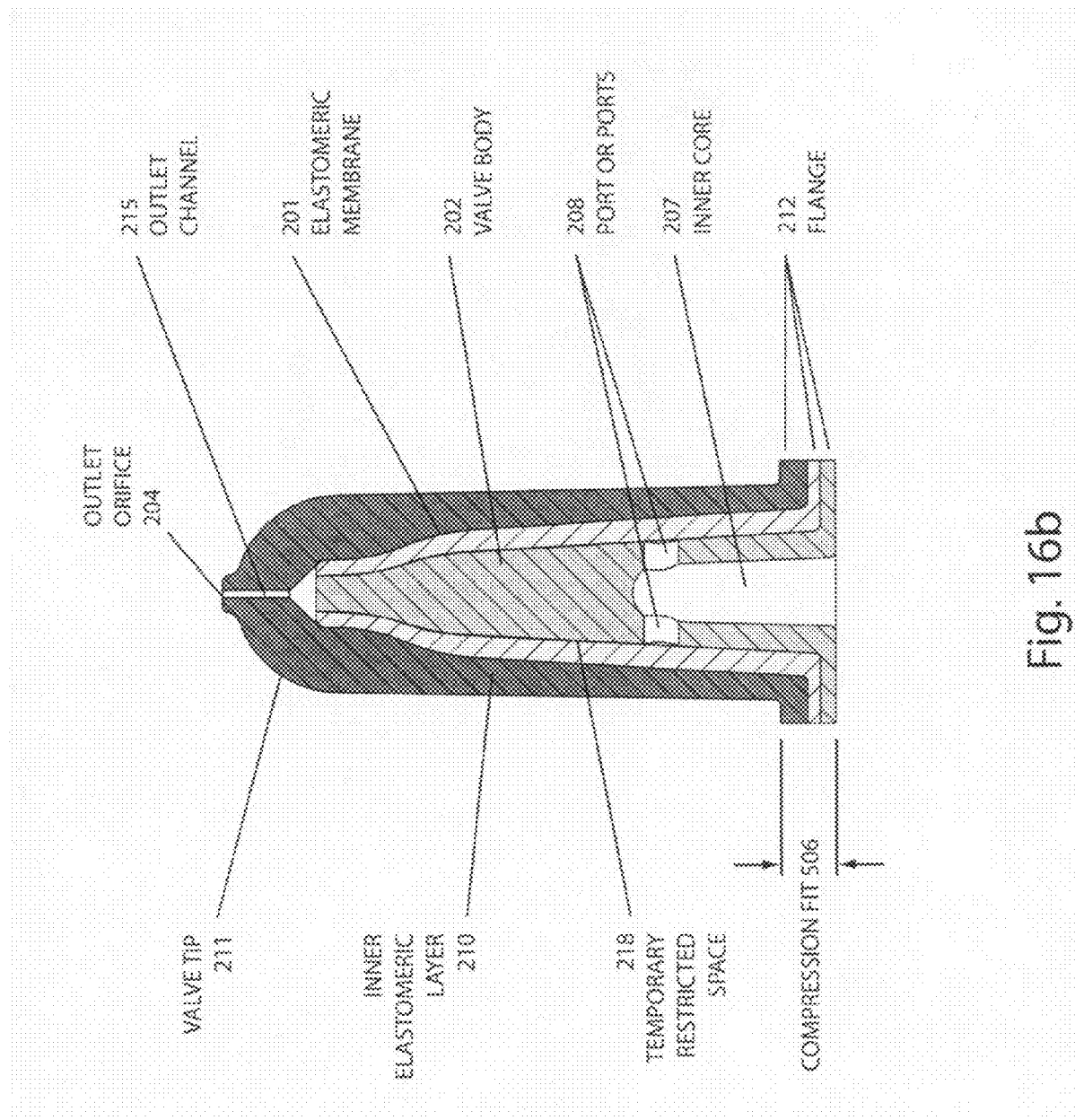
FIG. 16b depicts the alternate exemplary embodiment of FIG. 16a without a rigid cover.
Figure 16C:
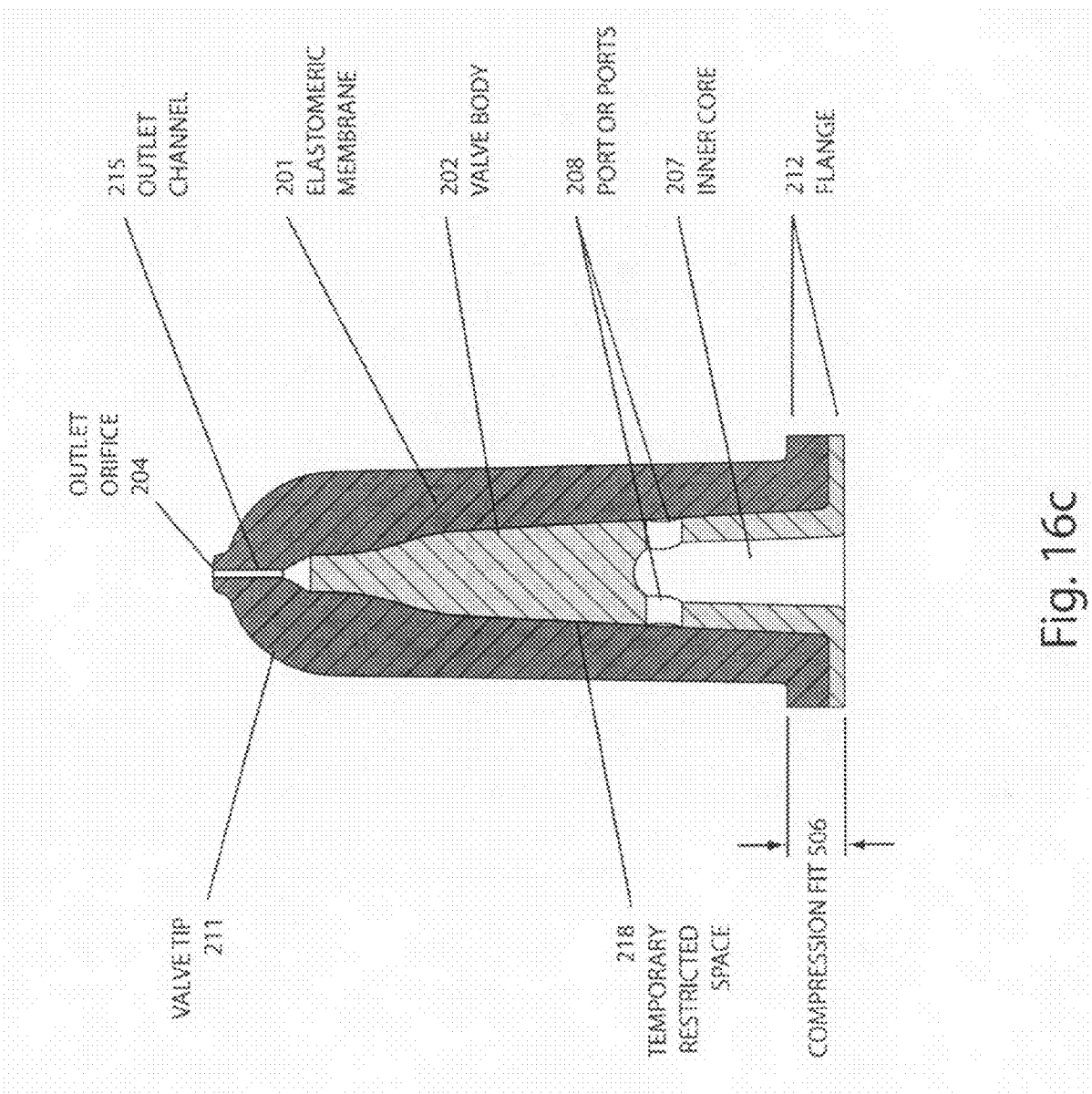
FIG. 16c depicts the alternate exemplary embodiment of FIG. 16a where the valve core is covered by a single elastomeric cover.

FIG. 16 show various exemplary embodiments of the one-way valve assembly 200 without the use of a clear space 206 (as shown, for example in FIG. 12a). Because no clear space 206 is used, there is no need for vent openings 213 (FIGS. 12a and 12b) and thus manufacture is much simpler. Because there is no defined air pocket for elastomeric membrane 201 to expand into as temporary restricted space 218 is created, a greater pressure may need to be applied to the flowable substance, depending upon its viscosity. Such greater pressures can be provided, for example, by a hydraulic (piston type) pump. To further simplify manufacture, FIGS. 16b and 16c depict various integrations that can be made in exemplary embodiments of the present invention. FIG. 16b depicts an exemplary embodiment where no outer cover is used, and thus the inner elastomeric layer 210 is expanded. FIG. 16c depicts a further integration over that of FIG. 16b, where both the elastomeric membrane 201 and the valve cover 209 have been integrated into the inner elastomeric layer 210, which now comprises the only other part of the valve assembly besides the valve body 202. The embodiments of FIGS. 16b and 16c thus obviate the need for the outer cover, and thus obviate the need for complex over-molding in manufacture.

In exemplary embodiments of the present invention, the material used for one or more of soft elastomeric valve tip 211, valve cover 209 and elastomeric membrane 201, can be made bacteriostatic, bactericidal, or both. For example, these materials can have a controlled amount of anti-microbial ingredients integrally molded, impregnated, or otherwise placed within the component, such as, silver ions contained within a ceramic carrier, or sustained-release ionic silver compounds, to provide at least a 3-log(99.9%) and as much as a 5 log(9.9.999%) reduction of colony-forming bacteria, fungi, yeast, molds, and other similar microbial contaminants. In exemplary embodiments of the present invention, silane-based, triclosan-based, or other anti-microbial agents suitable for compounding with or coating plastics can be used, for example, to achieve an equivalent reduction of contaminants. Additionally, in exemplary embodiments of the present invention, soft elastomeric valve tip 211, elastomeric membrane 201, valve cover 209, or any or all of them if desired, can (i) be positively charged so as to repel residual flowable substance 100, (ii) be hydrophobic by being coated in, for example, Teflon type-plastics, (iii) have decreased surface tension, (iv) be anti-wetting, or (v) any combination of the above, so as to repel the flowable substance 100 therefrom.

Additionally, other components of the delivery system can be made, or treated to be, bacteriostatic, bactericidal, or both, as may be desired. For example, as an extra precaution, all or a portion of the enclosing housing in which volume reducing reservoir 500 (FIG. 1) is encased or shielded can be bacteriostatic, bactericidal, or both, inasmuch as this is the portion of the delivery system that a user would hold, and thus where any germs on a user's fingers or hand would be in frequent contact with.

Thus, in exemplary embodiments of the present invention, the purity and/or sterility of the contents can be maintained in a multi-dose, preservative-free delivery system during use-life. Using, for example, applicable industry standards, antimicrobial properties of an exemplary delivery system can deliver up to, for example, a 99.999% (5-log) reduction in colony-forming capability within as little as 2 hours of exposure, which consistently eliminates any exterior tip contamination during use-life.

Thus, in exemplary embodiments of the present invention, a variety of pharmaceuticals, cosmetics, food stuffs and other flowable materials can be dispensed where it is important to maintain them free of contaminants from the ambient atmosphere. In specific exemplary embodiments of the present invention, the characteristics of the flowable substance 100 used, its density and viscosity, frictional forces between it and the inner surface of pumping chamber 301 and inner core 207, the size of metered volumes to be dispensed, and other specifications (surface area, sharpness of edge, flatness or concavity or convexity, level of polishing or smoothness) will be context specific (and, in fact, often customer specified) and will determine the type, material and dimensionality of one way dispensing valve assembly 200, dispensing pump 300, check valve 400 and volume reducing reservoir 500.

As noted, in exemplary embodiments of the present invention, various flowable substances, including pharmaceuticals, both prescription and over the counter, nutraceuticals and cosmeceuticals, can be safely dispensed in multi-dose preservative-free formulations, in a sterile manner, using various embodiments of the present invention as delivery systems. Exhibit A provides a non-comprehensive exemplary list of pharmaceuticals that can be so dispensed using exemplary embodiments of the present invention. It is noted that some of the pharmaceuticals listed currently only exist in preparations that do contain preservatives. These can obviously be reformulated in preservative-free preparations given the use of delivery systems according to exemplary embodiments of the present invention.

The above-presented description and figures are intended by way of example only and are not intended to limit the present invention in any way except as set forth in the following claims. It is particularly noted that the persons skilled in the art can readily combine the various technical aspects of the various exemplary embodiments described.

Exhibit A

A. Antiglaucoma Preparations and Miotics

| | |
|---|---|
| Sympathomimetics drugs are substances that mimic the effects of the hormone epinephrine (adrenaline) and the hormone/neurotransmitter norepinephrine (noradrenaline). They increase outflow of aqueous humor through trabecular meshwork and possibly through uveoscleral outflow pathway, probably by a beta2-agonist action. | Apraclonidine Brimonidine Clonidine Dipivefrine Epinephrine |
| Parasympathomimetics drugs act by stimulating or mimicking the parasympathetic nervous system (PNS). These chemicals are also called cholinergics because acetylcholine (ACh) is the neurotransmitter used by the PNS. They work by contraction of the ciliary muscle, tightening the trabecular meshwork and allowing increased outflow of the aqueous humour. | Aceclidine Acetylcholine Carbachol Demecarium Echothiophate Fluostigmine Neostigmine Paraoxon Physostigmine Pilocarpine |
| Carbonic anhydrase inhibitors lower secretion of aqueous humor by inhibiting carbonic anhydrase in the ciliary body. | Acetazolamide Brinzolamide Diclofenamide Dorzolamide Methazolamide |
| Beta blocking agents block the action of endogenous catecholamines epinephrine (adrenaline) and norepinephrine (noradrenaline) in particular, on β-adrenergic receptors. They decrease aqueous humor production by the ciliary body. | Befunolol Betaxolol Carteolol Levobunolol Metipranolol Timolol |
| Prostaglandin analogues increase uveoscleral outflow of aqueous humor. | Latanoprost (Xalatan, Pfizer) Bimatoprost (Lumigan, Allergan) Travoprost (Travatan, Alcon) Unoprostone (Rescula, Santen) |
| Other agents | Dapiprazole Guanethidine |

B. Preservative-Free Formulations—Various Uses:

| | |
|---|---|
| DRY EYE | a) 3-Dimensional Hyaluronic Acid (3D-HA) matrix with increased lubricant activity and anti-irritant activity generic in multi-dose preservative-free delivery systems (PF) |
| GLAUCOMA | a) Timolol generic in multi-dose preservative-free delivery systems (PF) |
| | b) Timolol with 3D-HA in multi-dose preservative-free delivery systems (PF) |
| | c) Brinzolamide with 3D-HA in multi-dose preservative-free delivery systems (PF) |
| | d) Xalatan using an emulsifier to eliminate BAK in multi-dose preservative-free delivery systems (PF) |
| ANTI-ALLERGY EYECARE | a) Chromeline (cromoglicic acid) with 3D-HA in multi-dose preservative-free delivery systems (PF) |
| ANTI-INFLAMMATORY EYECARE | a) NSAID Suprofenac with improved bioavailability in multi-dose preservative-free delivery systems (PF) |
| LENS CARE | a) Multi-purpose solution with 3D-HA for lens care in multi-dose preservative-free delivery systems (PF) |
| | b) Solution for daily disposable lenses with 3D-HA in multi-dose preservative-free delivery systems (PF) |
| | c) Rewetting solution with 3D-HA in multi-dose preservative-free delivery systems (PF) |
| | d) Lens Maintenance Solution and a Lens Rinsing Solution for Daily Lenses for Teenagers and Athletes of all ages in multi-dose preservative-free delivery systems (PF) |
| RHINOLOGY | a) Hyaluronic Acid based saline solution to moisten the mucosa of the nose in multi-dose preservative-free delivery systems (3D-HA based saline) |
| | b) Hyaluronic Acid based vasodilator containing solution for nasal decongestion in multi-dose preservative-free delivery systems (3D-HA based saline) |
| WOMEN'S HEALTH | a) Hyaluronic Acid (3D-HA) based anti-fungal ointment containing PHMB; propyleneglycol-free product in multi-dose preservative-free delivery systems |

-continued b) Personal/Sexual lubricant (A water-based cream containing PHMB and 2 non-irritating hypo-allergic ingredients)

C. Additional Products by Type, Activity Commercial Name and Manufacturer

| Type and Functionality | International Product | Active Ingredient(s) | Corporation |
|---|---|---|---|
| Prostaglandin analogues increase uveoscleral outflow of aqueous humor | Xalatan | latanoprost | PFIZER |
| | Lumigan | bimatoprost | ALLERGAN |
| | Travatan | travoprost | ALCON |
| | Xalacom | latanoprost, timolol | PFIZER |
| | Rescula | unoprostone | SANTEN |
| Beta blocking agents decrease aqueous humor production by the ciliary body. They block the action of endogenous catecholamines epinephrine (adrenaline) and norepinephrine (noradrenaline) in particular, on β-adrenergic receptors. Carbonic anhydrase inhibitors lower secretion of aqueous humor by inhibiting carbonic anhydrase in the ciliary body. Global Dry Eye Syndrome (DES) Products | Cosopt | timolol dorzolamide | MERCK & CO |
| | Blocadren | timolol | MERCK & CO |
| | Timoptol | timolol | SANTEN |
| | Betoptic | betaxolol | ALCON |
| | Timolol | timolol | ALCON |
| | Mikelan | carteolol | OTSUKA |
| | Hypadil | nipradilol | KOWA |
| | Rysmon | timolol | KISSEI YAKUHIN |
| | Carteol | carteolol | B&L |
| | Azopt | brinzolamide | ALCON |
| | Trusopt | dorzolamide | MERCK & CO |
| | Diamox | acetazolamide | BARR PHARMA |
| Other Polymers that retent water on the cornea | Celluvisc | Carboxymethylcellulose Sodium | ALLERGAN |
| | Refresh | Carboxylmethylcellulose Sodium | ALLERGAN |
| | Mytear | combo | SENJA PHARMA |
| | Systane | Polyethylene Glycol 400, Propylene Glycol | ALCON |
| | Refresh Tears | Carboxymethylcellulose Sodium | ALLERGAN |
| | Genteal | Carboxymethylcellulose Sodium, Hypromellose | NOVARTIS |
| | Tears Naturale | Hydroxypropyl Methylcellulose, Dextran 70, Glycerin | ALCON |
| | Viscotears | Carbomer | NOVARTIS |
| | Isopto Naturale | Hydroxypropyl Methylcellulose, Dextran 70 | ALCON |
| | Artelac | Hydroxypropyl Methylcellulose | B&L |
| | Rohto | Povidone | ROHTO CORP |
| | Refresh Liquigel | Carboxymethylcellulose Sodium | ALLERGAN |
| | Hypromellose | Hydroxypropyl Methylcellulose | VARIOUS GENERICS |
| Active Pharmaceutical Ingredients, small molecules | Restasis | Cyclosporin | ALLERGAN |
| | Smile Lion | Vitamin A, E, B, Potassium L-aspartate Tetrahydrozoline hydrochloride, Chlorpheniramine maleate, Neostigmine methylsulfate | LION |
| Hyaluronic Acid, polymers that retent water on cornea | Hyalein | Hyaluronic acid | SANTEN |
| | Opelead | Hyaluronic acid | SENJA PHARMA |
| | Hylo Comod | Hyaluronic acid | URSAPHARM |
| Balanced Salt Solution | Soft Santear | BSS, potassium, sodium | SANTEN |
| Surfactant | Lacri-lube | Mineral Oil, White Petrolatum | ALLERGAN |

What is claimed:

1. A delivery system for pure or sterile substances, comprising:
   a continuously sealing one way dispensing valve assembly, comprising:
   a valve body with an inner core;
   one or more ports provided in the valve body;
   an elastomeric membrane tightly covering the valve body and the one or more ports; and
   an axially extending valve cover, extending distally beyond said inner core; and
   an outlet channel,
   a dispensing pump;
   a check valve; and
   a reservoir,
   wherein the valve assembly is communicably connected to the dispensing pump, the dispensing pump communicably connected to the check valve, and the check valve communicably connected to the volume reducing reservoir,
   wherein the inner core within the valve body terminates in a three dimensional surface, whose perimeter intersects a distal end of the one or more ports.

2. The delivery system of claim 1, wherein said secure sealed flowpath is arranged to isolate and protect the pure or sterile substance contained within from ingress of external contaminants.

3. The delivery system of claim 1, wherein the components comprising the sealed flowpath are made with one or more materials that create a barrier to external contamination, including at least one of bacteriostatic and/or bactericidal materials and coatings.

4. The delivery system of claim 1, wherein the delivery system materials and assembly methods are arranged to provide a barrier against moisture vapor or oxygen penetration.

5. The delivery system of claim 4, wherein said assembly methods include at least one of thermosealed welds, interference or press fits, two-shot molding or overmolding, compression fits, ultrasonically welded assembly, and adhesive bonding.

6. The delivery system of claim 1, wherein the dispensing pump comprises a pumping chamber, appropriately sized to dispense a metered volume of a pure or sterile substance.

7. The delivery system of claim 1, wherein the pumping chamber comprises opposing surfaces with matched contours to provide intimate contact during actuation.

8. The delivery system of claim 1, wherein the pumping chamber is actuated by an actuator to displace a specific volume of flowable substance out through the check valve into the chamber.

9. The delivery system of claim 8, wherein said actuator is ergonomically configured as one of a button, paddle and button feature on a paddle.

10. The delivery system of claim 8, wherein the actuator provides a 1:1 or greater force upon the pumping chamber.

11. The delivery system of claim 8, wherein the actuator is configured as an extended overhanging paddle to provide a mechanical advantage of at least 2:1.

12. The delivery system of claim 1, further comprising a septum that creates a portal to and a sealed barrier between the outer environment and the portion of said flowpath within said reservoir and proximal to said check valve.

13. The delivery system of claim 1, wherein said pure or sterile substance is a preservative-free multi-dose formulation of a pharmaceutical, nautraceutical or cosmeceutical.

14. The delivery system of claim 13, wherein said pure or sterile substance is a preservative-free anti-glaucoma medication or miotic.

15. The delivery system of claim 1, wherein the continuously sealing one way dispensing valve assembly further comprises an outlet orifice.

16. The delivery system of claim 15, wherein the valve cover comprises a rigid outer layer and a flexible inner elastomeric layer.

17. The delivery system of claim 16, wherein said valve cover is manufactured using double shot molding such that the rigid outer layer is more durable than the inner elastomeric layer.

18. The delivery system of claim 15, wherein at least one of (i) said one or more ports, (ii) said elastomeric membrane, (iii) said outlet channel, and (iv) said outlet orifice are at least one of bacteriostatic, bactericidal, or both.

19. The delivery system of claim 15, wherein said one or more ports are at least one of: perpendicular to a central axis of the valve body, angularly skewed relative to the central axis of the valve body, formed with an inclined sloping edge at their distal end, and staggered along the central axis of the valve body.

20. The delivery system of claim 15, wherein the angulation of said one or more ports is articulated so as to direct flow in a helical manner towards the outlet channel.

21. The delivery system of claim 15, wherein the inner core is arranged to either (i) extend distally beyond the one or more ports, or (ii) terminate substantially at the distal end of the one or more ports.

22. The delivery system of claim 15, wherein the outlet orifice further comprises a concave termination at its tip through which the pure or sterile substance is dispensed.

23. The delivery system of any of claim 22, wherein the concave termination is sized and shaped to achieve an appropriate surface tension relative to the viscosity of the pure or sterile substance.

24. The delivery system of claim 22, wherein the outlet channel is tapered to control the velocity of the flowable substance as it is dispensed.

25. The delivery system of claim 15, further comprising at least one vent that provides air communication between atmospheric pressure and a space between the outer surface of the elastomeric membrane and the inner surface of the valve cover.

26. The delivery system of claim 25, wherein said vents are at least one of (i) protrusions in a side of the axially extending valve cover and a space arranged between radially protruding flanges of the elastomeric membrane and the valve cover.

27. The delivery system of claim 15, wherein at least one of:
 (i) the distal surfaces of the elastomeric membrane are arranged so as to be in intimate physical contact with the inner surface of the valve tip, so as to confine and direct the entirety of the pure or sterile substance through the outlet orifice;
 (ii) the outlet channel is tapered over its length, from a narrow restrictive proximal entrance aperture to a larger distal exiting aperture so as to slow the velocity of a substance passing through it;
 (iii) the outlet channel is tapered over its length, from a narrow restrictive proximal entrance aperture to a larger distal exiting aperture so as to slow the velocity of a substance passing through it,
 (iv) the outlet orifice is an aperture sized for optimal expulsion of a desired volume of the pure or sterile substance.

28. The delivery system of claim 15, further comprising a removable over cap, wherein said overcap is treated, embedded or coated with anti-microbial ingredients.

29. The delivery system of claim 15, wherein said elastomeric membrane is one of (i) assembled onto the valve body, and (ii) over-molded directly onto the valve body using a non-bonding separable polymer with molding shrinkage to achieve a tight and intimate shrink fit.

30. The delivery system of claim 29, wherein the tightness of the fit of the elastomeric membrane over the outer surface of the valve body can be made significantly high so as to insure proper resealing, while at the same time not be so high so as to make it impractically difficult for a user to push a substance through the valve.

31. The delivery system of claim 30, wherein the elastomeric membrane is made to fit one of (i) relatively tightly over the valve body for dispensing viscous flowable substances and (ii) relatively less tightly for dispensing individual droplets of aqueous fluids.

32. The delivery system of claim 1, wherein the elastomeric membrane is continuously sealing.

33. The delivery system of claim 32, wherein, under positive, pressure applied to the pure or sterile substance, a temporary restricted passageway is created between (i) an outer surface of the valve body and (ii) an inner surface of the elastomeric membrane, so as to allow the pure or sterile substance to exit from and be dispensed through the outlet channel and outlet orifice.

34. The delivery system of claim 33, wherein the temporary restricted passageway is immediately closed and sealed over its length against ingress of external contaminants through the temporary flowpath upon the absence of positive pressure on the pure or sterile substance.

35. The delivery system of claim 32, wherein the elastomeric membrane varies in thickness distally, being either (i) thicker at its distal end and thinner at its proximal end, or (ii) thinner at its distal end and thicker at its proximal end.

36. The delivery system of claim 32, wherein the continuously sealing, one way dispensing valve assembly further comprises a soft elastomeric valve tip.

37. The delivery system of claim 36, wherein said soft elastomeric valve tip is at least one of bacteriostatic, bactericidal, or both.

38. The delivery system of claim 36, wherein the one way dispensing valve assembly further comprises a nipple feature that protrudes beyond the valve tip.

39. The delivery system of claim 38, wherein the nipple feature comprises a terminating surface feature.

40. The delivery system of claim 39, wherein the terminating surface feature is adjacent to and co-axially surrounds the outlet orifice, and protrudes away from surrounding surfaces.

41. The delivery system of claim 39, wherein the terminating surface feature has a distinct edge and minimal surface area.

42. The delivery system of claim 39, wherein the terminating surface feature is made from hydrophobic materials to minimize surface tension so as to freely release the expelled volume of pure or sterile substance with minimal or no residual amount adhering to the nipple feature.

43. The delivery system of claim 1, wherein the outer surface of the distal end of the elastomeric membrane is arranged to have a mating, Fit with the receiving receptacle bore.

44. The delivery system of claim 1, wherein at least one of:
   (i) the elastomeric membrane tightly fits over the valve body in an interference percentage of between 2% and 10%, or
   (ii) a clear space is provided between the exterior of the elastomeric membrane and the interior of the valve cover.

45. The delivery system of claim 1, wherein the three dimensional surface is convex, with an apex offset distally from the distal end of the one or more ports.

46. A delivery system for pure or sterile substances, comprising:
   a continuously sealing one way dispensing valve assembly, comprising:
   a valve body with an inner core;
   at least two ports provided in the valve body;
   an elastomeric membrane tightly fitting over the valve body and the one or more ports; an axially extending valve cover; and
   an outlet channel,
   a dispensing pump;
   a check valve; and
   a reservoir,
   wherein the valve assembly is communicably connected to the dispensing pump, the dispensing pump communicably connected to the check valve, and the check valve communicably connected to the volume reducing reservoir,
   wherein the inner core within the valve body ends terminates in a three dimensional surface, provided at a distal end of the one or more ports.

47. The delivery system of claim 46, wherein the three dimensional surface is convex, with an apex offset distally from the distal end of the one or more ports.

48. The delivery system of claim 46, wherein at least one of:
   (i) the elastomeric membrane tightly fits over the valve body in an interference percentage of between 2% and 10%, or
   (ii) a clear space is provided between the exterior of the elastomeric membrane and the interior of the valve cover.

49. The delivery system of claim 46, wherein the three dimensional surface is convex, with an apex offset distally from the distal end of the one or more ports.

* * * * *